(12) United States Patent
Salahieh et al.

(10) Patent No.: US 11,376,061 B2
(45) Date of Patent: Jul. 5, 2022

(54) ENERGY DELIVERY DEVICE AND METHODS OF USE

(71) Applicant: Covidien LP, Mansfield, MA (US)

(72) Inventors: Amr Salahieh, Saratoga, CA (US); Tom Saul, Saratoga, CA (US)

(73) Assignee: Covidien LP, Mansfield, MA (US)

( * ) Notice: Subject to any disclaimer, the term of this patent is extended or adjusted under 35 U.S.C. 154(b) by 501 days.

(21) Appl. No.: 14/391,641

(22) PCT Filed: Mar. 15, 2013

(86) PCT No.: PCT/US2013/032431
§ 371 (c)(1),
(2) Date: Oct. 9, 2014

(87) PCT Pub. No.: WO2013/154775
PCT Pub. Date: Oct. 17, 2013

(65) Prior Publication Data
US 2015/0066013 A1 Mar. 5, 2015
US 2016/0374748 A9 Dec. 29, 2016

Related U.S. Application Data

(63) Continuation-in-part of application No. 14/348,035, filed as application No. PCT/US2012/057967 on Sep. 28, 2012, now abandoned.
(Continued)

(51) Int. Cl.
*A61B 18/14* (2006.01)
*A61B 18/00* (2006.01)
*A61B 90/00* (2016.01)

(52) U.S. Cl.
CPC .......... *A61B 18/14* (2013.01); *A61B 18/1492* (2013.01); *A61B 2018/0022* (2013.01);
(Continued)

(58) Field of Classification Search
CPC .... A61B 2018/1405; A61B 2018/1435; A61B 5/6853; A61B 2018/0022; A61B 2018/00238
See application file for complete search history.

(56) References Cited

U.S. PATENT DOCUMENTS 5,239,999 A 8/1993 Imran
5,330,496 A 7/1994 Alferness
(Continued)

FOREIGN PATENT DOCUMENTS

CN 106572881 4/2017
EP 2645955 10/2013
(Continued)

OTHER PUBLICATIONS

International Search Report and Written Opinion dated Apr. 10, 2013 in International Application No. PCT/US2012/057967.
(Continued)

*Primary Examiner* — Michael F Peffley
*Assistant Examiner* — Bo Ouyang
(74) *Attorney, Agent, or Firm* — Shumaker & Sieffert, P.A.

(57) ABSTRACT

The present disclosure is directed to an expandable energy delivery assembly adapted to deliver electrical energy to tissue. The assembly includes an elongate device including an irrigation shaft defining a irrigation lumen fluidly couplable to an irrigation source and a rapid exchange shaft defining a guidewire lumen configured for reception and passage of a guidewire. The assembly also includes an inflatable element that is secured to the elongate device. The inflatable element includes a double helical electrode disposed on the inflatable element that makes between about 0.5 to about 1.5 revolutions around the inflatable element.

20 Claims, 17 Drawing Sheets

Related U.S. Application Data

(60) Provisional application No. 61/622,495, filed on Apr. 10, 2012, provisional application No. 61/541,765, filed on Sep. 30, 2011, provisional application No. 61/593,147, filed on Jan. 31, 2012.

(52) U.S. Cl.
CPC ............... *A61B 2018/00083* (2013.01); *A61B 2018/00434* (2013.01); *A61B 2018/00577* (2013.01); *A61B 2018/00821* (2013.01); *A61B 2018/1435* (2013.01); *A61B 2090/3966* (2016.02); *A61B 2218/002* (2013.01)

(56) References Cited

U.S. PATENT DOCUMENTS

| | | | |
|---|---|---|---|
| 5,482,037 A | | 1/1996 | Borghi |
| 5,653,684 A | | 8/1997 | Laptewicz et al. |
| 5,902,251 A | * | 5/1999 | vanHooydonk ....... A61B 18/18 600/549 |
| 6,123,718 A | * | 9/2000 | Tu ...................... A61B 18/1492 606/41 |
| 6,190,382 B1 | * | 2/2001 | Ormsby ............. A61B 18/1492 606/33 |
| 6,405,732 B1 | * | 6/2002 | Edwards ............ A61B 18/1477 128/898 |
| 6,425,877 B1 | | 7/2002 | Edwards |
| 6,488,673 B1 | * | 12/2002 | Laufer .................. A61B 18/00 604/516 |
| 6,551,309 B1 | * | 4/2003 | LePivert ................ A61B 18/02 606/20 |
| 6,554,827 B2 | | 4/2003 | Chandresekara et al. |
| 7,959,628 B2 | | 6/2011 | Schaer et al. |
| 8,909,316 B2 | | 12/2014 | Ng |
| 9,050,106 B2 | | 6/2015 | Hill et al. |
| 9,084,609 B2 | | 7/2015 | Smith |
| 9,192,435 B2 | | 11/2015 | Jenson |
| 2003/0050637 A1 | * | 3/2003 | Maguire ................ A61B 18/00 606/41 |
| 2005/0015084 A1 | | 1/2005 | Hill, III et al. |
| 2005/0171525 A1 | | 8/2005 | Rioux et al. |
| 2005/0288730 A1 | | 12/2005 | Deem et al. |
| 2006/0210605 A1 | * | 9/2006 | Chang .................... A61B 17/24 424/434 |
| 2007/0106293 A1 | | 5/2007 | Oral et al. |
| 2007/0129720 A1 | * | 6/2007 | Demarais ............. A61N 1/0551 606/41 |
| 2007/0203549 A1 | * | 8/2007 | Demarais ................ A61N 1/05 607/72 |
| 2009/0024195 A1 | | 1/2009 | Rezai et al. |
| 2009/0248012 A1 | * | 10/2009 | Maor ................. A61B 18/1492 606/41 |
| 2010/0004650 A1 | * | 1/2010 | Ormsby ............. A61B 18/1492 606/41 |
| 2010/0160906 A1 | * | 6/2010 | Jarrard ............... A61B 18/1492 606/33 |
| 2010/0204560 A1 | | 8/2010 | Salahieh et al. |
| 2010/0222851 A1 | | 9/2010 | Deem et al. |
| 2010/0262140 A1 | * | 10/2010 | Watson ................ A61B 1/0008 606/41 |
| 2011/0306851 A1 | * | 12/2011 | Wang ................... A61B 5/4893 600/301 |
| 2011/0319809 A1 | | 12/2011 | Smith |
| 2012/0029511 A1 | * | 2/2012 | Smith ................ A61B 18/1492 606/41 |
| 2012/0071870 A1 | | 3/2012 | Salahieh et al. |
| 2012/0310233 A1 | * | 12/2012 | Dimmer ............. A61B 18/1492 606/33 |
| 2014/0243821 A1 | * | 8/2014 | Salahieh .................. A61N 1/05 606/41 |
| 2014/0316398 A1 | * | 10/2014 | Kelly ..................... A61B 18/02 606/24 |
| 2015/0025525 A1 | * | 1/2015 | Willard .................. A61B 18/16 606/34 |
| 2015/0066013 A1 | | 3/2015 | Salahieh et al. |
| 2015/0080882 A1 | * | 3/2015 | Skinner ............. A61M 25/1002 606/41 |
| 2015/0105659 A1 | * | 4/2015 | Salahieh ............ A61B 18/1492 600/435 |
| 2015/0223866 A1 | | 8/2015 | Buelna et al. |
| 2015/0223877 A1 | | 8/2015 | Behar et al. |
| 2015/0289770 A1 | | 10/2015 | Wang |
| 2016/0175040 A1 | | 6/2016 | Magana et al. |
| 2016/0175582 A1 | | 6/2016 | Serna et al. |
| 2016/0374568 A1 | | 12/2016 | Wang |
| 2017/0042610 A1 | | 2/2017 | Smith et al. |

FOREIGN PATENT DOCUMENTS

| | | |
|---|---|---|
| EP | 2709517 | 3/2014 |
| EP | 2836151 | 2/2015 |
| EP | 2839802 | 2/2015 |
| EP | 2890321 | 7/2015 |
| EP | 2907464 | 8/2015 |
| EP | 3003191 | 4/2016 |
| EP | 3049007 | 8/2016 |
| EP | 3102132 | 12/2016 |
| EP | 3123973 | 2/2017 |
| EP | 3138521 | 3/2017 |
| EP | 3148467 | 4/2017 |
| EP | 3157455 | 4/2017 |
| JP | 6122217 | 4/2017 |
| WO | WO-198603129 A1 | 6/1986 |
| WO | WO-199510319 A1 | 4/1995 |
| WO | WO-2001022897 A1 | 4/2001 |
| WO | WO-2009121017 A1 | 10/2009 |
| WO | WO-2010057043 A1 | 5/2010 |
| WO | WO-2011075328 A1 | 6/2011 |
| WO | WO-2011130534 A2 | 10/2011 |
| WO | WO-2015161181 | 10/2015 |
| WO | WO-2015183952 | 12/2015 |
| WO | WO-2015196169 | 12/2015 |

OTHER PUBLICATIONS

International Search Report and Written Opinion dated Jul. 17, 2013 in International Application No. PCT/US2013/032431.
International Search Report and Written Opinion for PCT/US2013/032454 dated Apr. 13, 2012.
Prosecution History from U.S. Appl. No. 14/348,035, dated Mar. 27, 2014 through Aug. 21, 2018, 117 pp.
U.S. Appl. No. 17/188,833, filed Mar. 1, 2021, naming inventors Salahieh et al.

\* cited by examiner

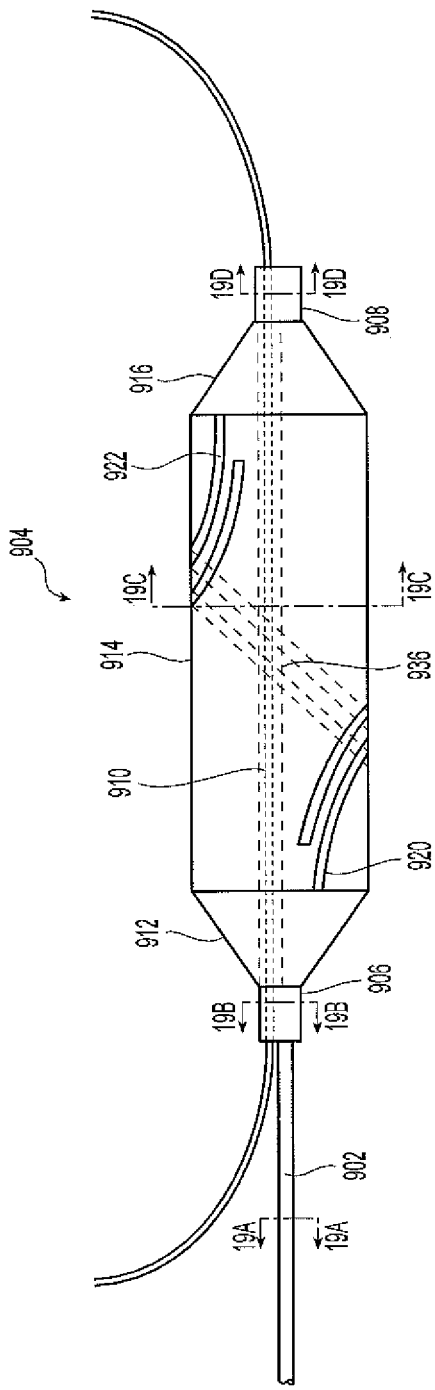
*Fig. 18*
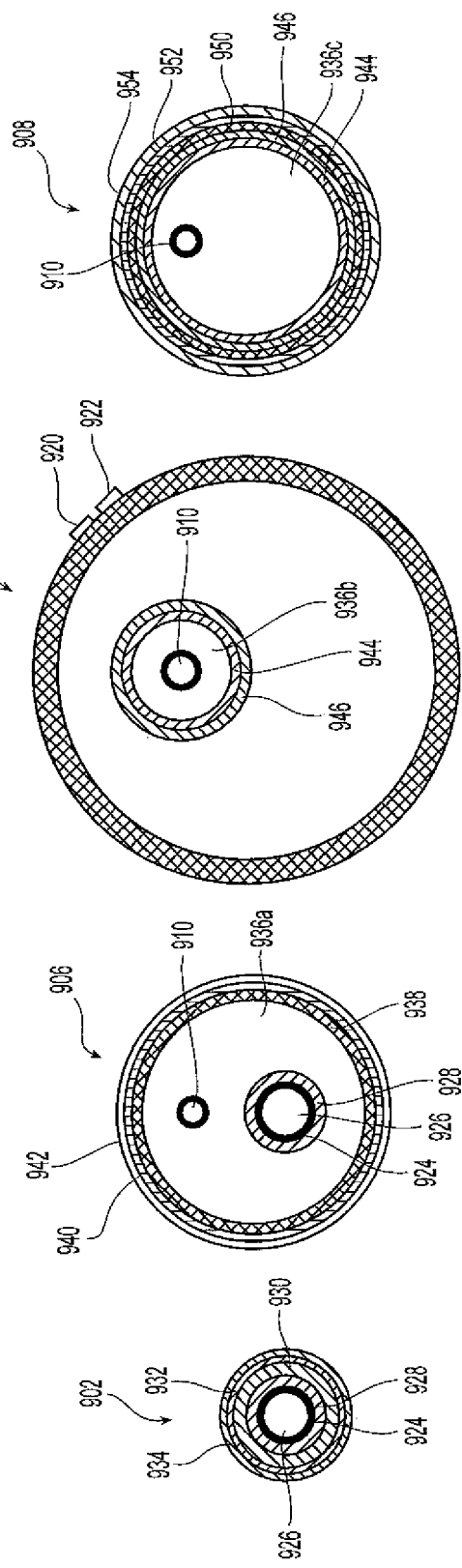
*Fig. 19A*
*Fig. 19B*
*Fig. 19C*
*Fig. 19D*

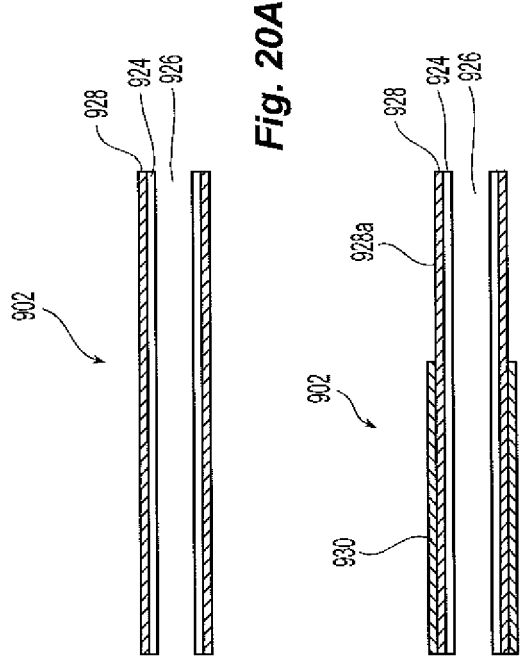
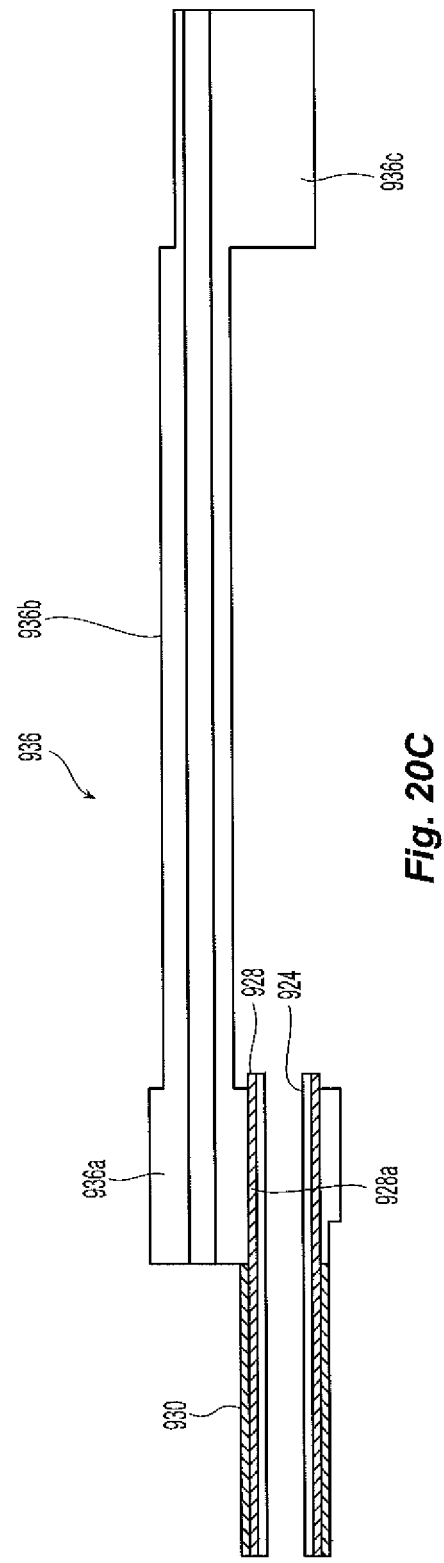

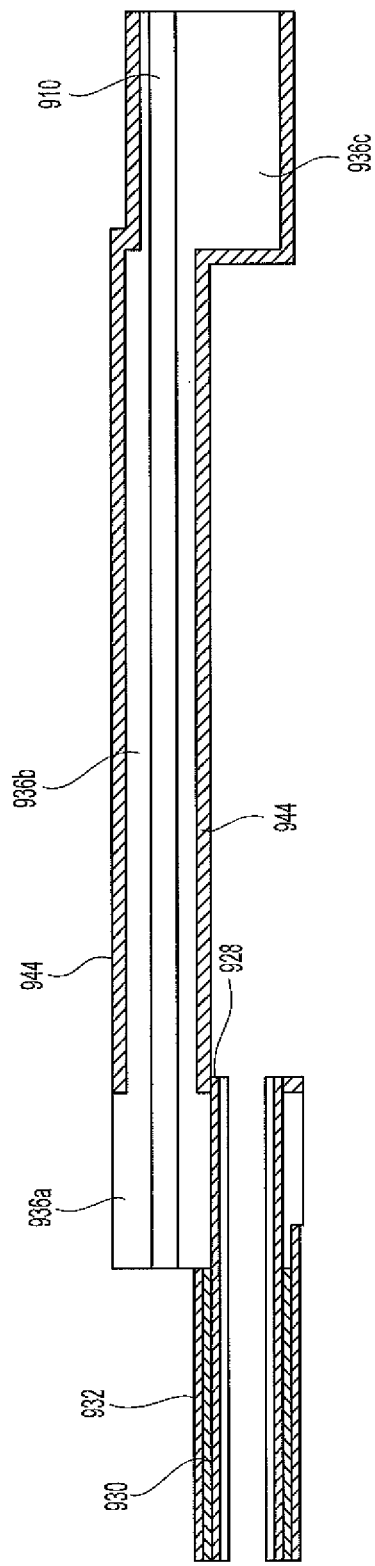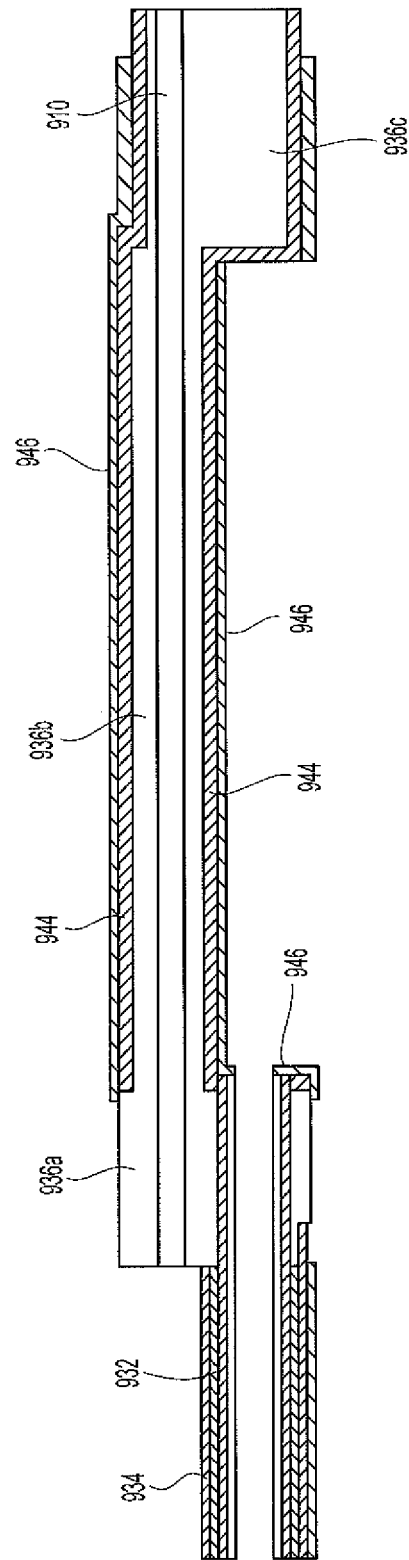

ENERGY DELIVERY DEVICE AND METHODS OF USE

CROSS REFERENCE TO RELATED APPLICATIONS

The present application is a national stage entry of PCT/US2013/032431, filed Mar. 15, 2013, which claims the benefit of, and priority to, U.S. Provisional Application Ser. No. 61/622,495 filed Apr. 10, 2012. The present application is also a continuation-in-part of U.S. patent application Ser. No. 14/348,035, filed Mar. 27, 2014; which is a national stage entry of International Application No PCT/US2012/057967, filed Sep. 28, 2012; which claims the benefit of U.S. Provisional Patent Application Ser. No. 61/593,147 filed Jan. 31, 2012 and U.S. Provisional Patent Application Ser. No. 61/541,765, filed Sep. 30, 2011. The entire contents of each of these applications are incorporated herein by reference. This application is also related to and incorporates by reference herein the complete disclosures of the following patent applications: U.S. Provisional Pat. App. No. 61/113,228, filed Dec. 11, 2008; U.S. Provisional Pat. App. No. 61/160,204, filed Mar. 13, 2009; U.S. Provisional Pat. App. No. 61/179,654, filed May 19, 2009; U.S. Pat App. Pub. No. 2010/0204560, filed Nov. 11, 2009; U.S. Provisional Pat. App. No. 61/334,154, filed May 12, 2010; U.S. patent application Ser. No. 13/106,658, filed May 12, 2011.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure relates generally to medical devices and methods and more particularly to devices and methods for applying radiofrequency energy to tissue.

BACKGROUND ART

Some medical treatment procedures involve the disruption of a region of tissue. For example, medical treatment procedures include the delivery of energy to disrupt a region of tissue. Radiofrequency ("RF") energy devices are an example of devices that can be used to perform such medical treatments.

Some RF energy devices have a single RF energy element or a plurality of discrete RF energy elements that have to be repeatedly moved within the subject in order to apply sufficient RF energy to the entire region of the tissue. Such RF energy devices may need to be moved within a patient during a given procedure, which can increase the complexity, time, and energy required to perform a given procedure.

DISCLOSURE OF INVENTION

In an aspect of the present disclosure, an expandable energy delivery assembly adapted to deliver electrical energy to tissue is provided. The assembly includes an elongate device including an irrigation shaft having a proximal end and a distal end and defining a irrigation lumen fluidly couplable to an irrigation source at the proximal end of the irrigation shaft. The assembly also includes a rapid exchange shaft having a proximal end and a distal end and defining a guidewire lumen configured for reception and passage of a guidewire, the proximal end of the rapid exchange shaft overlapping the distal end of the irrigation shaft. The assembly also includes an inflatable element having a proximal end and a distal end, the proximal end of the inflatable element secured to the elongate device where the proximal end of the rapid exchange shaft overlaps the distal end of the irrigation shaft, and the distal end of the inflatable element secured to the elongate device at the distal end of the rapid exchange shaft. The inflatable element includes a double helical electrode disposed on the inflatable element, the double helical electrode making between about 0.5 to about 1.5 revolutions around the inflatable element. In alternative embodiments the inflatable element includes a single helical electrode thereon.

In some embodiments, the double helical electrode makes between about 1 to about 1.25 revolutions around the inflatable element.

In some embodiments, the elongate device includes a first conductive layer and a second conductive layer. The first conductive layer is disposed on substantially the entire irrigation shaft and the second tubular member and the second conductive layer is disposed over the first conductive layer on substantially the entire irrigation shaft. A first insulation layer is disposed between the first conductive layer and the second conductive layer on substantially the entire irrigation shaft.

In some embodiments, the double helical electrode includes a first helical electrode electrically coupled to the first conductive layer and a second helical electrode electrically coupled to the second conductive layer. The first conductive layer and the first helical electrode form a first unitary conductive layer without an electrical junction, and the second conductive layer and the second helical electrode form a second unitary conductive layer without an electrical junction.

In some embodiments, the first conductive layer, the second conductive layer, and the double helical electrode are an elastomeric ink.

In some embodiments, the inflatable element has a proximal transition section covered with a third conductive layer that electrically couples the second helical electrode and the second conductive layer on the elongate device and a distal transition section covered with a fourth conductive layer. The fourth conductive layer electrically couples the first helical electrode and the first conductive layer on the elongate device. A second insulation layer may be disposed on the third conductive material and the fourth conductive material.

In some embodiments, the inflatable element is a balloon with a substantially cylindrical section and the double helical electrode is disposed on the substantially cylindrical section.

In some embodiments, the distal end of the irrigation shaft is disposed within the inflatable element such that the irrigation lumen and the interior of the inflatable element are fluidly coupled.

In some embodiments, the inflatable element includes at least one irrigation aperture. The at least one irrigation aperture may be in the inflatable element, the helical electrode, anywhere but the helical electrode, or adjacent the helical electrode.

In some embodiments, the double helical electrode is electrically coupled to an energy source.

In another aspect of the present disclosure, a method of manufacturing an expandable energy delivery assembly adapted to deliver energy to tissue is provided. The method includes applying a conductive material on an irrigation shaft to form a first conductive layer and applying an insulation material on the first conductive layer while keeping a distal portion of the first conductive layer exposed to form a first insulation layer. A rapid exchange shaft is attached to the irrigation shaft over the distal portion of the first conductive layer and a conductive material is applied on the rapid exchange shaft to form a second conductive layer that is electrically coupled to the first conductive layer. A conductive material is applied on the first insulation layer to form a third conductive layer and an insulation material is applied to the second conductive layer and the third conductive layer to form a second insulation layer. The second insulation layer being applied in a manner such that a distal portion of the second conductive layer is exposed and a distal portion of the third conductive layer is exposed. An inflatable element is attached to the first tubular member and the second tubular member and a conductive material is applied to a proximal transition section of the inflatable element to form a proximal electrode such that the third conductive layer is electrically coupled to the proximal electrode. A conductive material is applied to a distal transition section of the inflatable element to form a distal electrode such that the second conductive layer is electrically coupled to the distal electrode. A conductive material is applied to the inflatable element to form a double helical electrode having a first helical electrode and a second helical electrode wherein the first helical electrode is electrically coupled to the proximal electrode and the second helical electrode is coupled to the distal electrode.

In some embodiments, the inflatable element is an inflatable balloon.

In some embodiments, the conductive material is elastomeric ink. The conductive material may be applied using one of the following processes: vapor deposition, electroplating, electroless plating, pad printing, spraying, and ink jet.

In some embodiments, the step of applying the conductive material to the inflatable element to form the double helical electrode includes inflating the inflatable element and applying the conductive material on an exterior surface of the inflatable element to form the double helical electrode making between about 0.5 and about 1.5 revolutions around the inflatable element. A mask may be applied to the inflatable element before applying the conductive material on the exterior surface of the inflatable element.

BRIEF DESCRIPTION OF DRAWINGS

FIG. 18 illustrates a side view of the energy delivery device of FIG. 17;

FIGS. 19A-19D illustrate cross-sections of the energy delivery device of FIG. 18;

FIGS. 20A-20H illustrate a method of manufacturing an energy delivery device with a rapid exchange configuration according to an embodiment of the present disclosure.

DETAILED DESCRIPTION

Figure 1A:
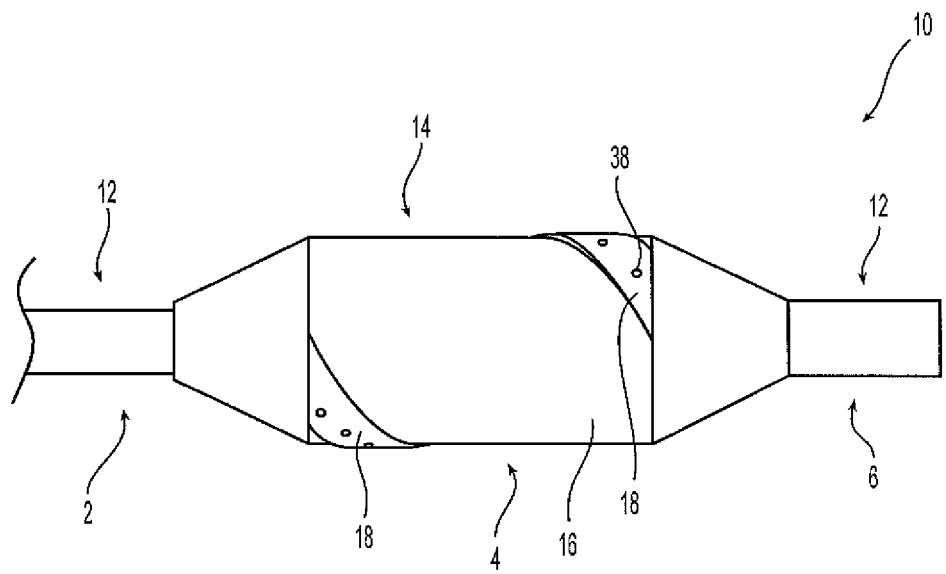
FIGS. 1A, 1B, and 2 illustrate a portion of an energy delivery device comprising a helical electrode on an expandable element according to an embodiment of the present disclosure.

Particular embodiments of the present disclosure are described hereinbelow with reference to the accompanying drawings; however, the disclosed embodiments are merely examples of the disclosure and may be embodied in various forms. Like reference numerals may refer to similar or identical elements throughout the description of the figures.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the terms proximal and distal refer to a direction or a position along a longitudinal axis of a catheter or medical instrument. The term "proximal" refers to the end of the catheter or medical instrument closer to the operator along the length of the device, while the term "distal" refers to the end of the catheter or medical instrument closer to the patient along the length of the device. For example, a first point is proximal to a second point if it is closer to the operator end of the catheter or medical instrument than the second point. The measurement term "French", abbreviated Fr or F, is defined as three times the diameter of a device as measured in mm. Thus, a 3 mm diameter catheter is 9 French in diameter. The term "operator" refers to any medical professional (i.e., doctor, surgeon, nurse, or the like) performing a medical procedure.

One aspect of the disclosure is a RF delivery device that is adapted to deliver RF energy to tissue. FIG. 1A illustrates a side view of a distal region of RF delivery device 10. Device 10 has proximal region 2, intermediate region 4, and distal region 6. Device 10 includes an elongate portion 12 and expandable portion 14 (shown in an expanded configuration) disposed on a distal region of elongate portion 12. Expandable portion 14 includes inflatable element 16 on which conductive material 18 is disposed.

Figure 1B:
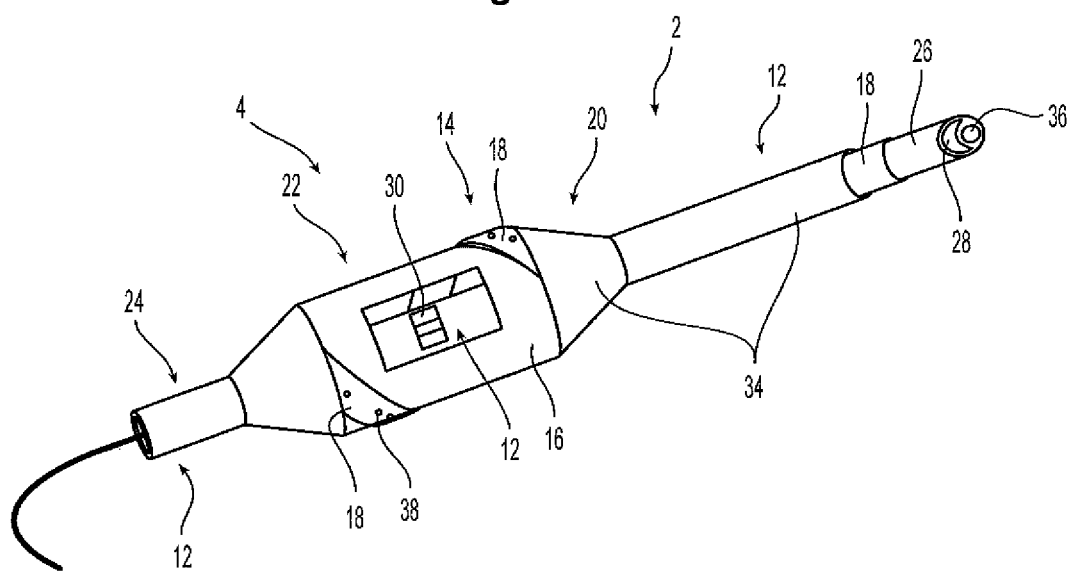

FIG. 1B illustrates a perspective view of the portion of the device shown in FIG. 1A, with a rectangular section of inflatable element 16 removed to illustrate elongate portion 12 disposed inside inflatable element 16.

Figure 2:
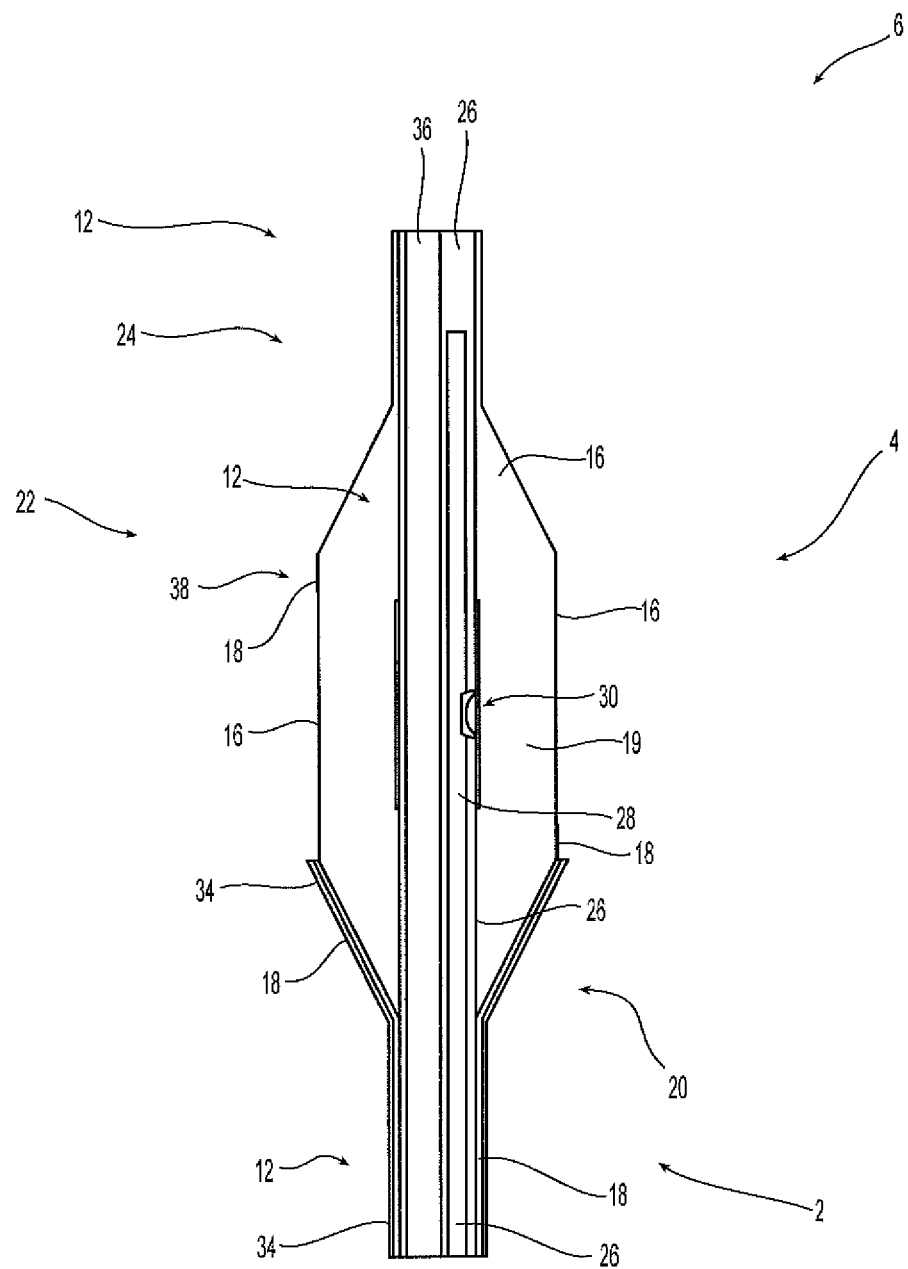

FIG. 2 shows a sectional view of the portion of the device shown in FIG. 1A. Expandable portion 14 includes a proximal transition section 20, intermediate section 22, and distal transition section 24. Proximal transition section 20 and distal transition section 24 are shown with conical configurations extending towards elongate portion 12 but are not limited to this configuration. Intermediate section 22 is substantially cylindrically-shaped when inflatable element 16 is in the expanded configuration shown in FIGS. 1A, 1B, and 2. The proximal end of inflatable element 16 and the distal end of inflatable element 16 are secured to catheter 26, which is part of elongate portion 12.

Conductive material 18 is disposed on catheter 26 proximal to the expandable portion 14, and it is also disposed on the cylindrical section of inflatable element 16 in a helical pattern forming a helical electrode 19 as shown. In proximal region 2 and in proximal section 20 of the expandable portion, insulation material 34 is disposed on the layer of conductive material 18. In the cylindrical intermediate section 22 of expandable portion 14, insulation material 34 is not disposed on the helical electrode, allowing energy to be delivered to tissue through conductive material 18. In the proximal region 2 of the device, and in proximal section 20 of expandable portion 14, conductive material 18 is covered with a layer of insulation, and thus energy is not applied to tissue in those areas. The conductive material that is not covered by dielectric material on the distal portion of the system is considered an electrode. The conductive material and the electrode are in this embodiment the same material.

The conductive material 18 is disposed on substantially the entire catheter 26 in proximal region 2 of the device. "Substantially the entire," or "substantially all," or derivatives thereof as used herein include the entire surface of catheter 26, but also includes most of the surface of the catheter. For example, if a few inches of the proximal end of catheter 26 are not covered with conductive material, conductive material is still considered to be disposed on substantially all of the catheter. The conductive material 18 and insulation material 34 extend 360 degrees around the catheter shaft, as opposed to only covering discrete lateral sections of the catheter. Alternatively, in some embodiments the conductor covers only a portion of the lateral surface of the catheter shaft. The conductive material and insulation material may cover the entirety or only a portion of the proximal transition section of the expandable portion. The insulation will typically cover the entirety of the conductive material in this region. The conductive material and insulation material could, however, also be disposed on the distal section 24 of expandable portion 14.

In some embodiments the helical electrode makes about 0.5 revolutions to about 1.5 revolutions around the inflatable element. The number of revolutions is measured over the length of the helical electrode. The electrode may extend from the proximal transition section to the distal transition section (as shown in FIG. 2), but the electrode may extend over any section of the inflatable element. For example, the proximal end of the electrode may be disposed distal to the proximal transition section, and the distal end of the electrode may be proximal to the distal transition section.

One revolution traverses 360 degrees around the longitudinal axis of the expandable element. One revolution of the electrode, along an end-view of inflatable device, forms a circle, although depending on the cross sectional shape of the expandable element, the electrode can form any variety of shapes in an end-view. An electrode making 0.5 revolutions therefore traverses one half of 360 degrees, or 180 degrees. An electrode making 0.5 revolutions has distal and proximal ends that are on opposite sides of the balloon. In an end-view of the inflatable element with a circular cross section, an electrode making 0.5 revolutions has a semicircular, or C, shape.

The proximal end of the electrode can be disposed anywhere on the expandable element and the distal end of the electrode can be anywhere on the expandable element, as long as the proximal end is proximal to the distal end. In some embodiments, the proximal end of the electrode is at the boundary between the proximal transition section and the cylindrical intermediate section of the expandable element, and the distal end of the electrode is at the boundary between the distal transition section and the cylindrical intermediate section. In other embodiments the proximal end of the electrode is disposed distal to the boundary between the proximal intermediate section and the cylindrical intermediate section of the expandable element, and the distal end is proximal to the boundary between the distal transition section and the central intermediate section of the expandable element. In these other embodiments the electrode is considered to extend along a subset of the length of the central intermediate section of the expandable element. In the embodiment shown in FIG. 1B, the electrode makes about 1 revolution around the inflatable element. In some embodiments the electrode makes about 0.5 revolutions around the inflatable element. In some embodiments the electrode makes about 0.75 revolutions around the inflatable element. In some embodiments the electrode makes about 1 revolution around the inflatable element. In some embodiments the electrode makes about 1.25 revolutions around the inflatable element. In some embodiments the electrode makes about 1.5 revolutions around the inflatable element.

The device is adapted to be coupled to an RF generator, which supplies RF current through the conductive material 18 on catheter 26 and inflatable element 16. In this manner RF current can be delivered to the desired tissue. Energy is thus applied to tissue in the configuration of the conductive material on the intermediate section 22 of the expandable portion 14, which in this embodiment is a helical, or spiral, configuration.

Figure 3A:
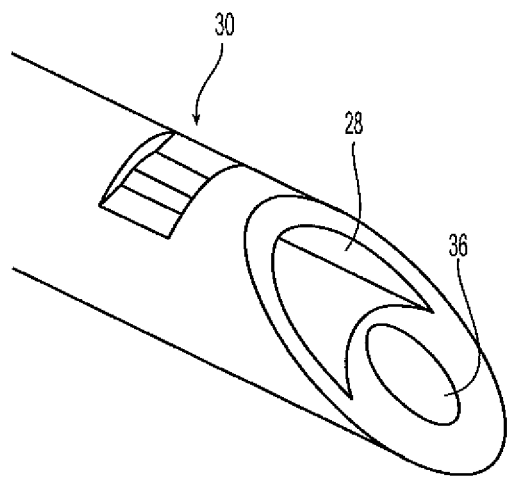
FIGS. 3A and 3B show a portion of an elongate device according to an embodiment of the present disclosure.
Figure 3B:
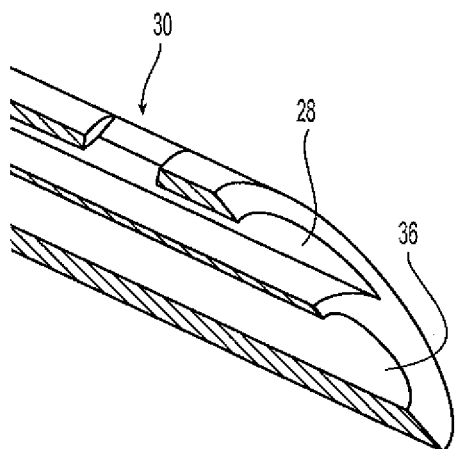

Within the expandable portion, catheter 26 is not covered with conductive material or insulation material. Catheter 26 includes guide element lumen 36 and inflation lumen 28, also referred to herein as irrigation lumen, extending therethrough. Guide element lumen 36 extends from the proximal end of the device (not shown) to the distal end. Irrigation lumen 28 extends from the proximal end of catheter 26 (not shown) to a location within inflatable element 16. Irrigation port 30 is located inside inflatable element 16 and is in between proximal and distal ends of irrigation lumen 28. Irrigation lumen 28 and irrigation port 30 provide for fluid communication between the irrigation lumen and the interior of inflatable element 16. FIGS. 3A and 3B illustrate additional views of guide element lumen 36, irrigation lumen 28, and irrigation port 30. In some embodiments catheter 26 ranges in size from 2 to 8 French, and in some embodiments is 4 Fr. In some embodiments the guide wire lumen is between 1 and 4 Fr and in some embodiments is 2.5 Fr.

Expandable portion 14 includes one or more irrigation apertures 38 to allow irrigation fluid to pass from inside inflatable element 16 to outside inflatable element 16. The irrigation apertures can be formed only in the electrode section of expandable portion 14 (see, for example, FIG. 1A), only in the non-electrode section of inflatable portion 14, or in both the electrode section and in the non-electrode section. The irrigation fluid is adapted to cool the conductive material 18 and/or tissue. The apertures allow for fluid to flow out of the balloon, allowing either a continuous or non-continuous supply of fluid from a fluid reservoir, through the lumen, and into the balloon. The irrigation fluid is in some embodiments cooled prior to delivery.

Figure 4:
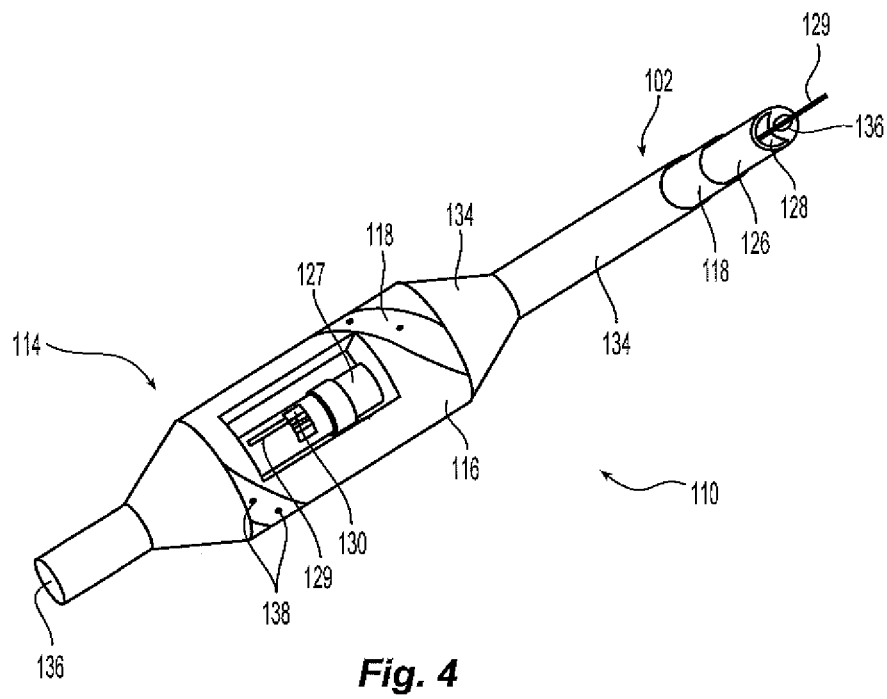
FIG. 4 shows a portion of an energy delivery device comprising a temperature sensor according to an embodiment of the present disclosure.

FIG. 4 illustrates a portion of an embodiment of a RF delivery device. Delivery device 110 is similar to the RF delivery device shown in FIGS. 1-3. Device 110 includes catheter shaft 126 covered with conductive material 118, upon which insulation material 134 is disposed. Insulation material 134 is also disposed on the proximal transition section of the expandable portion 114, similar to the embodiment shown in FIGS. 1-3. The inflatable element also has conductive material 118 disposed on the inflatable element in the form of a helical electrode. Catheter 126 has guiding element lumen 136 and irrigation lumen 128 therein. Device 110 also includes at least one marker 127 disposed on catheter 126 such that the marker is within expandable portion 114 (shown as a balloon). Device 110 also includes irrigation port 130 in fluid communication with irrigation lumen 134. Device 110 also includes temperature sensor 129, such as a thermocouple, a resistance temperature detector, or a thermistor, that is electrically coupled from the proximal end of the device (not shown) through irrigation lumen 128, out of irrigation port 130, and is secured at its distal region to catheter 126. The temperature sensor could alternatively be disposed on the inner or outer surface of inflatable element 116. In some embodiments marker 127 is a radio opaque marker comprised of Pt, Par, or other suitable radio opaque material. In some embodiments the marker may also comprise features viewable under fluoroscopy that allow for the visualization of the rotational orientation of the marker, and therefore the expandable section. This allows the physician to note the location of and/or realign the expandable element and helical electrode as necessary within the renal artery.

Figure 5:
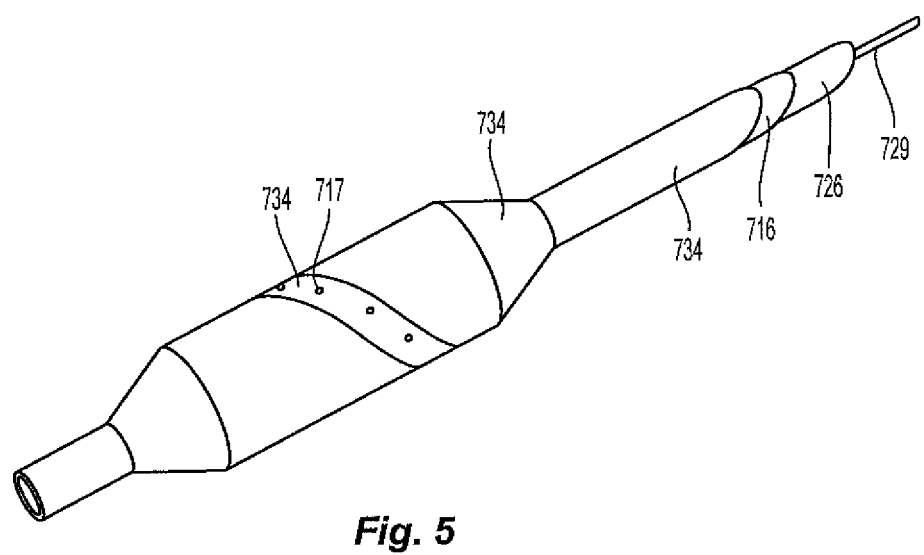
FIG. 5 illustrates a portion of an energy delivery device wherein portions of a helical electrode are covered with an insulation material according to an embodiment of the present disclosure.

The irrigation fluid is adapted to cool the electrode on the inflatable element. The irrigation fluid cools the RF electrode as it flows within the inflatable element and after it passes through the apertures as it flows across the outer surface of the inflatable element. Temperature sensor 129 is adapted to sense the temperature of the fluid within inflatable element 116. The signal from the temperature sensor may be used in a feedback control mechanism to control the flow of fluid from a fluid reservoir (not shown) into the inflatable element. Alternatively, the irrigation fluid may be delivered at a substantially constant rate and the signal from the temperature sensor used as a signal to automatically shut off the RF generator if the sensed fluid temperature is above a threshold limit, thereby terminating that portion of the procedure. Such a condition is considered a fault and after identification and resolution of a fault, a procedure may be restarted. FIG. 5 illustrates a delivery device in which portions of the helical conductor have been covered by insulation material 734, forming a plurality of discrete circularly-shaped windows surrounding apertures 717 on the electrical conductor. In this fashion a single conductor can be used to create a number of discrete burn zones following a helical path along and around a vessel wall.

Figure 6:
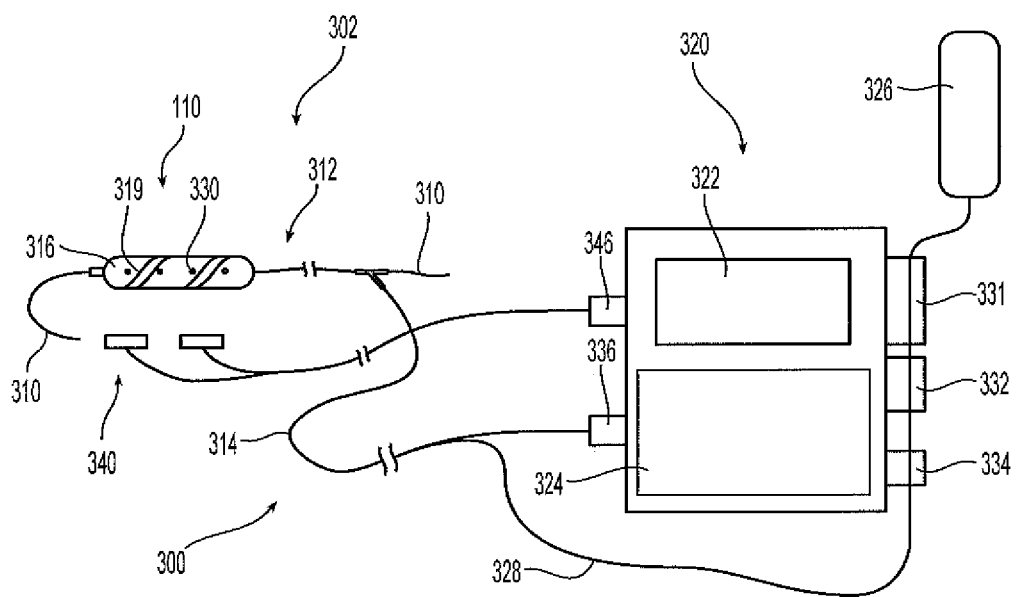
FIG. 6 illustrates a system for delivering energy to tissue according to an embodiment of the present disclosure.

One aspect of the disclosure is a system to delivery RF energy to treat tissue. FIG. 6 illustrates a system 300 adapted to deliver RF energy to treat tissue. System 300 includes RF energy delivery device 302, which can comprise any of the RF energy delivery devices described herein. Delivery device 302 is shown including inflatable element 316, helical energy delivery element 319, irrigation apertures 330, guidewire 310, and elongate member 312. System 300 also includes external housing 320, which includes display 322 and controller 324. Housing 320 includes connector 336, which is adapted to connect to instrument interface cable 314. System 300 also includes fluid reservoir 326, which is in fluid communication with delivery device 302 via irrigation line 328. The system also includes fluid pump 331, optional pressure sensor 332, and optional bubble sensor 334. System 300 also includes a grounding plate or set of grounding plates 340 interfaced to controller 324 via connector 346.

Figure 14:
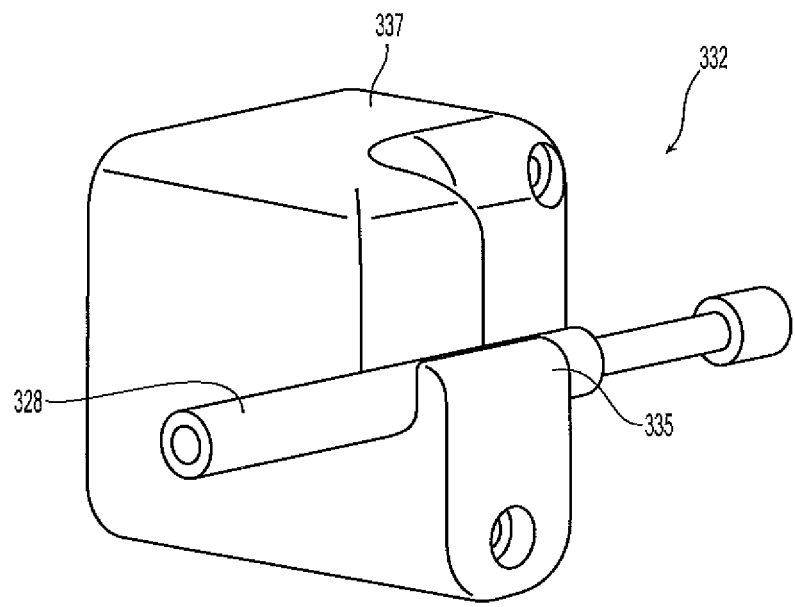
FIGS. 14 and 15 illustrate an embodiment of a pressure sensor according to an embodiment of the present disclosure.
Figure 15:
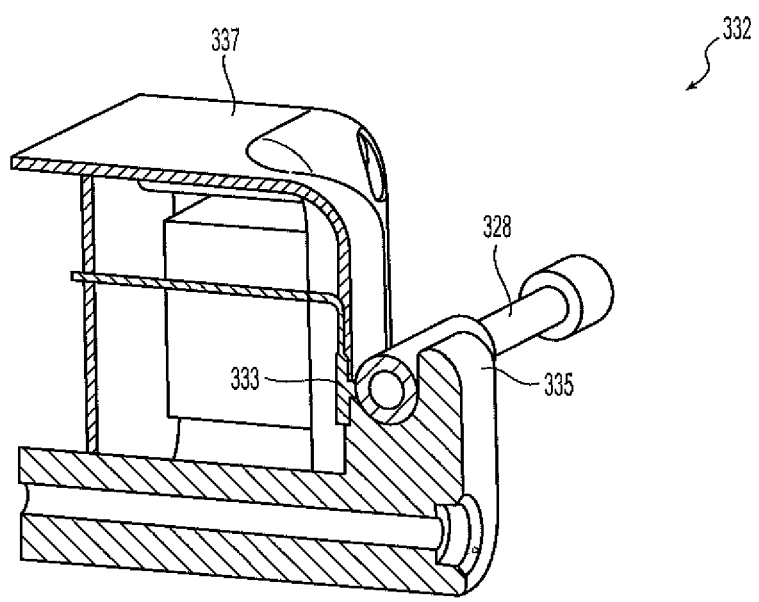

An embodiment of pressure sensor 332 from the system in FIG. 6 is shown in FIGS. 14 and 15. Pressure sensor 332 includes a housing, which comprises capture portion 335 and a force sensor 333. Capture portion 335 is configured to substantially surround irrigation tube 328. Additionally, capture portion 335 captures tubing 328 such that a portion of the wall of irrigation tube 328 is compressed against force sensor 333. The force experienced by the force sensor is then a function of the force associated by the compression of the irrigation tube and the pressure within the irrigation tube. In operation, a measurement is made under a no flow condition that describes the offset associated with the compression of the irrigation tube. This offset measurement is made prior to the initiation of a procedure and may be repeated at the beginning of each power cycle. This value is then used as an offset for subsequent measurements made under flow conditions. A force/pressure calibration per tubing type or per tube is then used to convert the force signal to a pressure value.

The disclosure includes methods of using any of the RF delivery devices and systems herein. In some embodiments the devices and/or systems are used to treat hypertension by disrupting the transmission within renal nerves adjacent one or both renal arteries.

The present methods control renal neuromodulation via thermal heating mechanisms. Many embodiments of such methods and systems may reduce renal sympathetic nerve activity. Thermally-induced neuromodulation may be achieved by heating structures associated with renal neural activity via an apparatus positioned proximate to target neural fibers. Thermally-induced neuromodulation can be achieved by applying thermal stress to neural structures through heating for influencing or altering these structures. Additionally or alternatively, the thermal neuromodulation can be due to, at least in part, alteration of vascular structures such as arteries, arterioles, capillaries, or veins that perfuse the target neural fibers or surrounding tissue.

Thermal heating mechanisms for neuromodulation include both thermal ablation and non-ablative thermal alteration or damage (e.g., via sustained heating or resistive heating). Thermal heating mechanisms may include raising the temperature of target neural fibers above a desired threshold to achieve non-ablative thermal alteration, or above a higher temperature to achieve ablative thermal alteration. For example, the target temperature can be above body temperature (e.g., approximately 37 degrees C.) but less than about 45 degrees C. for non-ablative thermal alteration, or the target temperature can be about 45 degrees C. or higher for the ablative thermal alteration.

The length of exposure to thermal stimuli may be specified to affect an extent or degree of efficacy of the thermal neuromodulation. For example, the duration of exposure can be as short as about 5, about 10, about 15, about 20, about 25, or about 30 seconds, or could be longer, such as about 1 minute, or even longer, such as about 2 minutes. In other embodiments, the exposure can be intermittent or continuous to achieve the desired result.

In some embodiments, thermally-induced renal neuromodulation may be achieved via generation and/or application of thermal energy to the target neural fibers, such as through application of a "thermal" energy field, including, electromagnetic energy, radiofrequency, ultrasound (including high-intensity focused ultrasound), microwave, light energy (including laser, infrared and near-infrared) etc., to the target neural fibers. For example, thermally-induced renal neuromodulation may be achieved via delivery of a pulsed or continuous thermal energy field to the target neural fibers. The energy field can be sufficient magnitude and/or duration to thermally induce the neuromodulation in the target fibers (e.g., to heat or thermally ablate or necrose the fibers). As described herein, additional and/or alternative methods and systems can also be used for thermally-induced renal neuromodulation.

The energy field thermally modulates the activity along neural fibers that contribute to renal function via heating. In several embodiments, the thermal modulation at least partially denervates the kidney innervated by the neural fibers via heating. This may be achieved, for example, via thermal ablation or non-ablative alteration of the target neural fibers.

In some uses in which RF energy is used to ablate the renal nerve, the RF delivery device is first positioned within one or more renal arteries and RF energy is delivered into renal nerves to disrupt the nerve transmission sufficiently to treat hypertension. The disruption pattern within the artery preferably extends substantially 360 degrees around the artery. Electrodes that treat tissue falling diametrically in a single plane normal or oblique to the longitudinal axis of the vessel have been shown to increase the risk of stenosing a vessel treated with RF energy. Spiral, or helical, patterns as described herein create patterns of treated tissue for which the projection along the longitudinal axis is circular and therefore have a high probability of treating any renal nerve passing along the periphery of the renal artery. The patterns, however, have minimal risk of creating a stenosis. Previous attempts have used a point electrode at a distal end or distal region of a device. In these attempts, the electrode is disposed in the renal artery followed by RF energy delivery. To disrupt renal nerve tissue in a non circumferential pattern using a point electrode, the device is first positioned within the renal artery adjacent arterial tissue. RF energy is then delivered to disrupt a region of renal nerve. The device must then be moved axially (distally or proximally) and rotated, followed by additional RF delivery. The movement and RF delivery is repeated in a pattern until the renal nerves have been sufficiently disrupted. The repeated movements are time consuming and increase the complexity of the overall process for the physician. During an emergency situation the physician may lose track of the position and sequence of previous burns thereby jeopardizing the likelihood of creating a pattern sufficient to treat the neural tissue or be forced to increase the number of burns thereby over-treating the patient.

Utilizing a single helical electrode as described herein provides procedural improvements over previous attempts. By using an electrode with the configuration of the desired treatment region, the device need not be moved to disrupt tissue in a desired treatment configuration. In particular the device need not be moved axially or rotated to treat an entire renal nerve treatment region. This reduces the overall time of the treatment. Additionally, this allows energy to be delivered to a desired treatment region in a variety of patients with much greater predictability. Additionally, if markers are used that allow for rotational alignment, the device may be moved and/or removed and then replaced and realigned, allowing the procedure to be restarted at a later time.

Figure 7:
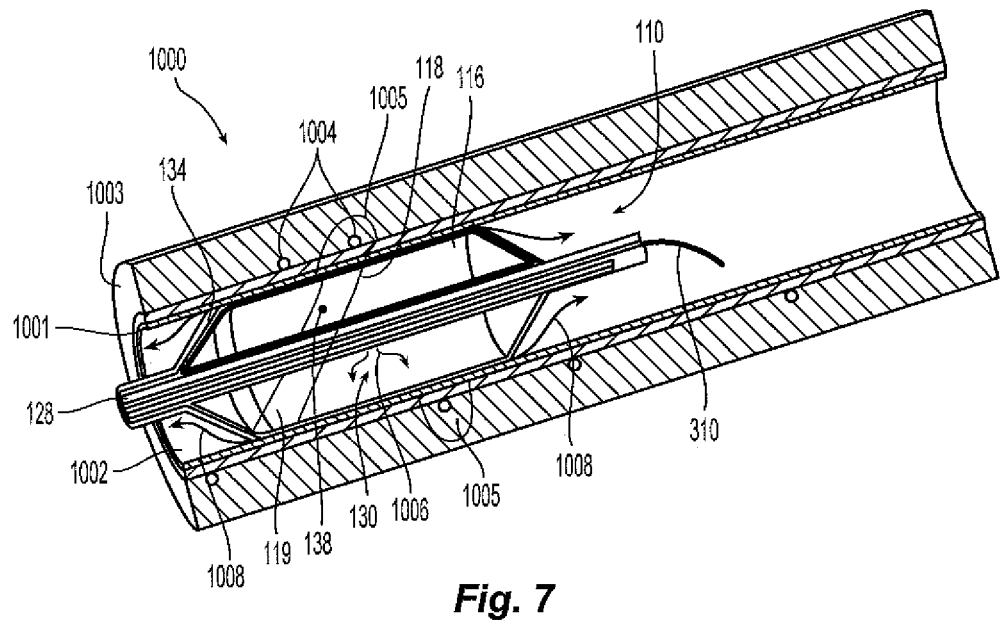
FIG. 7 illustrates a cross section of an energy delivery device with a helical electrode in use within a renal artery according to an embodiment of the present disclosure.

A method of using an RF delivery device to treat hypertension is shown in FIG. 7, and will be described using the device in FIG. 4 and the system shown in FIG. 6. The methods described herein can be carried out by other systems and by other RF delivery devices, such as the RF devices described herein.

The RF delivery device is positioned in a renal artery using a percutaneous access through a femoral artery. The expandable portion is delivered into the renal artery in a collapsed configuration (not shown). Once the expandable portion is in position, fluid from fluid reservoir 326 is pumped in an open loop control configuration, under constant flow, through irrigation line 328 and into inflatable element 116 by pump 330. Fluid flow into inflatable element 116 causes inflatable element 116 to expand. Device 110 in FIG. 7 is in a delivered, or expanded, configuration within renal artery 1000. The tunica intima 1001 is surrounded by the tunica media 1002, which is in turn surrounded by adventitial tissue 1003. Tissue renal nerves 1004 are shown within the adventitial, and some renal nerves not shown will be found within the tunica media.

The fluid continually passes through apertures 138 in the expandable portion as it is replaced with new fluid from fluid reservoir 326. Once fully expanded, the conductive material 118 on the inflatable element fully assumes the helical configuration, as shown in FIGS. 4 and 7. RF energy is then delivered to the helical electrode on the inflatable element. Control unit 324 controls the parameters of the RF alternating current being delivered through the conductive material on the catheter and the helical electrode on the inflatable element.

In general, the RF signal characteristics are chosen to apply energy to depths at which the renal nerves are disposed to effectively ablate the renal nerves. In general, the power is selected to ablate a majority of the renal nerves adjacent to where the device is positioned within the renal nerve. In some embodiments the tissue is ablated to a depth of between about 3 mm to about 7 mm from the tissue closest to the device in the renal artery.

The RF signal can have the following characteristics, but these are not intended to be limiting: the frequency is between about 400 KHz to about 500 KHz and is a sine wave; the power is between about 30 W to about 80 W, the voltage is between about 40 v and about 80 v; and the signal is an intermittent signal.

Tissue treated by the RF energy via the helical electrode comprised is shown as regions 1005, delineated by a dashed line. As illustrated, a region of treated tissue 1005 adjacent to the cut away section of conductor 118 includes nerve 1004. The device is shown being used in monopolar mode with a return electrode 340 positioned somewhere on the patient's skin.

Control unit 324 controls the operation of pump 330 and therefore controls the flow rate of the fluid from reservoir into the inflatable element. In some embodiments the pump is continuously pumping at constant flow rate such that the flow is continuous from the reservoir, as is illustrated in FIG. 7. In some embodiments the pump is operated in an open loop constant flow configuration where pump rate is not adjusted as a function of any control parameter other than an over-pressure condition sensed by pressure sensor 332, in which case RF power delivery is terminated, the pump is turned off, and an over-pressure condition reported to the operator. The pump is typically operated for a period of time which encompasses the delivery of the RF energy and turned off shortly after the conclusion of the procedure or if the pressure sensor senses an undesirable condition, discussed herein.

The irrigation fluid is delivered from the pump through irrigation line 328 to irrigation lumen 128 to irrigation port 130 into the inflatable element 116, and then out of the inflatable element through irrigation apertures 138. The pressure measured at the pressure sensor is driven by flow rate and the series sum of the fluid resistance of all of the elements in the fluid path. The choice of fluid flow rate is driven by the required cooling rate and limited by the amount of irrigant fluid that can be tolerated by the patient which is delivered during the sum of treatments cycles. The system is designed such that at the desired fluid flow there is a defined operating pressure within the inflatable element. An optimal inflatable element inflation pressure is a pressure that is sufficient to completely inflate the inflatable element such that the RF electrode engages the treatment tissue. The operating pressure within the inflatable element will be driven by the fluid flow, the number of apertures, and their cross sections. The distribution, number, and cross section of the irrigation apertures will be driven by the flow rate, the configuration of the electrode, the intended operating pressure, and the maximum desired exit velocity for the irrigation fluid. If the number of apertures is too small and the distribution too sparse some areas of the surface will not receive appropriate irrigation and thereby be subject to overheating and possible charring of tissue. For a set of circular apertures and a given flow rate, the mean exit velocity for the irrigation fluid will drop as the number of apertures is increased while decreasing the cross sectional area of each aperture such that the fluid resistance of the sum of apertures is appropriate to maintain the desired inflation pressure. Minimizing the irrigation fluid exit velocity minimizes or precludes the possibility that lesions will be eroded through the treatment tissue.

A set of operating conditions and design parameters is now provided, and is not meant to be limiting. An inflation pressure between about 0.5 atm and less than about 4 atm used with a noncompliant inflatable element of approximately 0.75 mil (~19 um) thick ensures tissue engagement in a renal artery. In some particular embodiments the inflation pressure is about 2 atm+/−0.5 atm. The irrigation fluid delivery rate is between about 1 mL/min and about 20 ml/min. In some particular embodiments the delivery rate is about 10 mL/min+/−2 mL/min. The expandable portion includes eight irrigation apertures about 2.6 mil (0.0026 inches) in diameter distributed on either side of the helical electrode and equally spaced along the edge of the electrode. In such a configuration the mean exit velocity is about 6 msec. In some embodiments the maximum mean fluid exit velocity is between about 1 m/sec and about 20 msec.

The above operating parameters are not intended to be limiting. For example, the inflation pressure can be between about 0.5 atm (or less) and about 10 atm, the flow rate can be between about 1 mL/min to about 50 mL/min, and any suitable number of apertures with any suitable size can be incorporated into the device. Apertures may be of the same size or of different sizes and may also be uniformly or non-uniformly distributed through and/or about the electrode. The apertures are sized such that the total resistance of the set of apertures is appropriate to maintain the pressures defined herein internal to the inflatable element at the desired flows described herein. Alternatively, the total resistance is such that the desired flows described herein are maintained at the desired pressures described herein. The total resistance for the parallel combination of apertures is calculated as the inverse of the sum of the inverses of the individual aperture resistances.

The system shown also includes pressure sensor 332, which is adapted to determine if the pressure rises above or below threshold limits. If the fluid pressure rises above an established limit, the controller shuts off the RF energy, and fluid pump 330 is automatically shut off. The pressure can elevate if one or more of the apertures become blocked, preventing fluid from passing out of the balloon, which can prevent the electrode from being cooled sufficiently. Controller 324 therefore runs fluid pump 330 in a binary manner, either open-flow or off.

The system as shown also includes a temperature sensor 129 secured to the catheter within the inflatable element. If the sensed temperature of the fluid is above a threshold limit, the fluid will not properly cool the electrode. If the sensed fluid temperature is above a threshold limit, control unit 324 is adapted to cease RF current delivery. The fluid temperature in the balloon can rise if one or more apertures are blocked, preventing the electrode from being properly cooled and also increasing the risk of charring. The fluid pressure generally will rise above a threshold limit if this occurs as well. In some embodiments the system has only one of the temperature sensor and pressure sensor.

The system may also include bubble sensor 334, which is adapted to sense bubbles in the fluid line and communicates with control unit 324 to shut off pump 330 if bubbles of sufficient volume are detected.

The system can also include a flow sensor to determine if the flow rate has gone below or above threshold limits. RF energy delivery is automatically stopped and the pump is automatically shut down if the flow rate goes above or below the threshold limits.

In an alternate embodiment to that of FIG. 6 the constant flow control of the system may be replaced by constant pressure control. In such a system the reservoir 326 may be maintained at a pressure within the prescribed pressure range using, for example without limitation, an IV bag pressure cuff or other suitable means, and the pump replaced by a flow sensor or flow controller. In such a system pressure is maintained at a substantially constant level within the prescribed range and flow rate monitored. When flow rate falls outside of the proscribed range the RF power delivery is terminated.

In general, using a greater number of smaller holes provides substantially the same resistance as a fewer number of larger holes, but mean fluid exit velocity is diminished.

Figure 8:
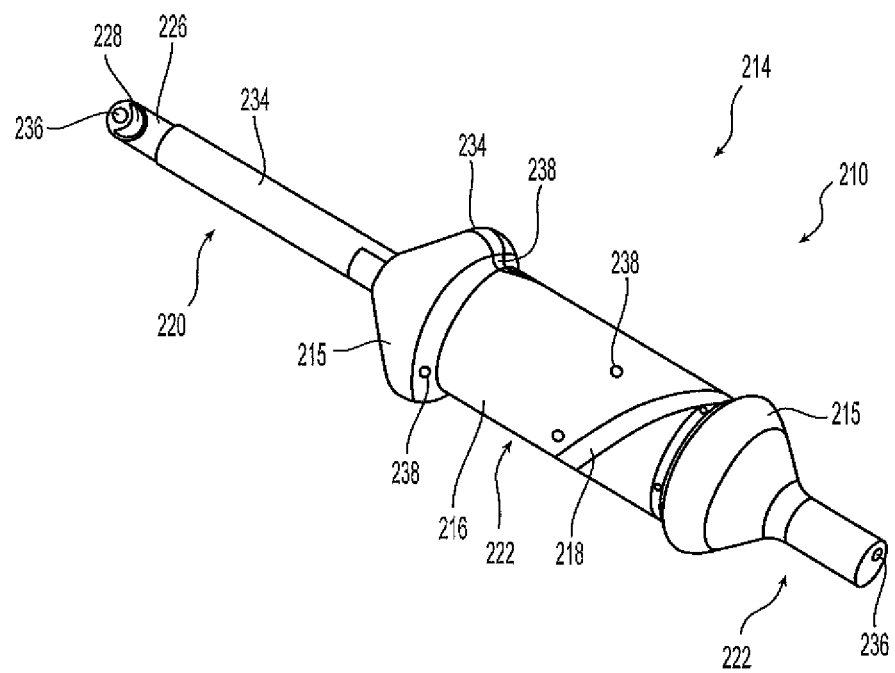
FIGS. 8 and 9 illustrate a portion of an energy delivery device wherein energy is delivered to renal nerves through conductive fluid to tissue according to an embodiment of the present disclosure.

FIG. 8 illustrates a portion of an embodiment of an RF delivery device wherein the expandable portion has a general dumbbell configuration, and energy is delivered through the conductive fluid to the tissue. RF delivery device 210 includes expandable portion 222 that comprises inflatable element 216 on which is disposed conduction material 218 with a helical configuration. The catheter has guiding element lumen 236 and irrigation lumen 228. A conductive layer and an insulation layer are disposed on the catheter as in the embodiment in FIGS. 1-5. The proximal and distal portions of inflatable element 216 have diameters that are greater than the intermediate section, such that the expandable portion has a general dumbbell shape. When inflated, larger diameter proximal and distal ends of the expandable portion 214 contact the vessel wall, while space is left between the cylindrical section 222 of the expandable element and the vessel wall as illustrated in FIG. 8. The irrigation fluid flowing through irrigation apertures 238 fills the space between the cylindrical section 222 and tissue, and current from the helical electrode is carried through the conductive irrigation fluid and into the adjacent tissue. In this configuration the helical electrode does not contact tissue directly, therefore the uniformity of heating is improved and the risk of charring or overheating the tissue is reduced.

Device 210 is also adapted to query the nervous tissues adjacent to the device, but need not include this functionality. Device 210 includes nerve conduction electrodes 215 located on the outer surface of the dumbbell shaped proximal and distal ends of the expandable portion 214. In use, an electrical signal, typically a low current pulse or group of pulses is transmitted to one of the conduction electrodes. This triggers a response in adjacent renal nerves, which then travels along the nerves and at some time "t" later is sensed by the opposite electrode when the signal is traveling in the appropriate direction. By alternating which electrode is used as the exciter and which the sensor, both changes in efferent and afferent nerve conduction in the renal nerves may be monitored as a function of RF treatments induced by the RF electrode. The conduction electrodes are wired to the sensing circuits in the controller via wires traveling within the catheter shaft, as in the irrigation lumen, or additional lumens (not shown), or multiple conductors may be applied to the outer surface of the shaft (not shown).

Figure 9:
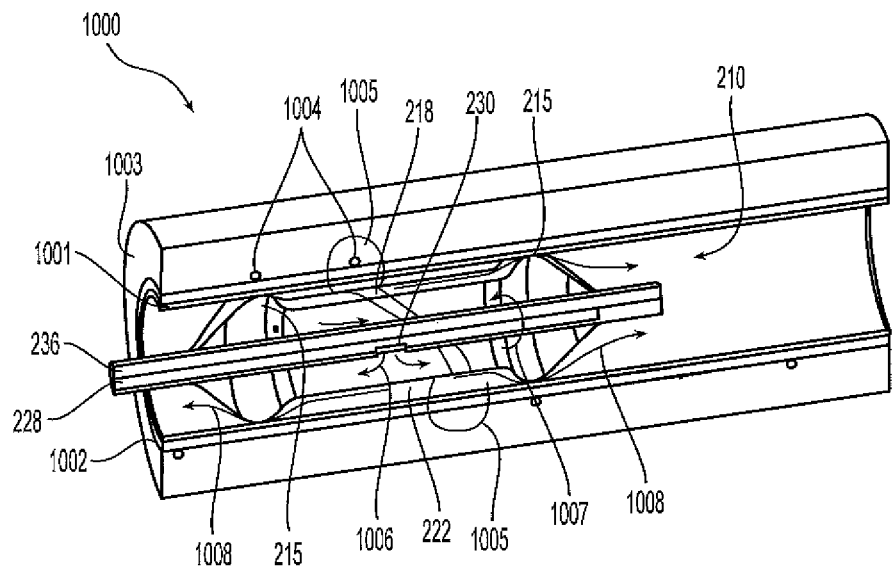

FIG. 9 illustrates the delivery device 210 in a delivered, or expanded, configuration within a renal artery. Areas 1005 indicate tissue treated by the application of RF energy delivered via the helical electrode. An area 1005 adjacent to conductor 218 surrounds a renal nerve 1004. Irrigation fluid movement is shown by the arrows. The fluid enters the inflatable element 216 at irrigation port 230 as shown by arrows 1006. The fluid then flows out of inflatable element 216 at irrigation apertures 238, shown by arrows 1007. The fluid then flows past conduction electrodes 215 into the blood stream, shown by arrows 1008.

In use, the dumbbell configuration creates a small space between the helical electrode and the arterial wall. The irrigation fluid, such as saline, can be used to act as a conductor and transfer energy from the electrode to the tissue. In such a system, the impedance variations, at the interface between the tissue and the electrode, associated with surface irregularities and variations in contact between the electrode and tissue will be minimized. In this manner the fluid can act both to cool the electrode and to transfer energy to tissue. The thin layer of fluid between the electrode and tissue can also prevent sticking and add lubrication.

Unless specifically stated to the contrary, the embodiment of FIG. 7 includes features associated with the embodiment from FIG. 4.

The configuration of RF delivery device 210 is less dependent on considerations listed above with respect to the embodiment in FIG. 4 as the irrigation fluid does not directly impinge on the treatment tissue and is allowed to circulate in the space between the vessel wall and the cylindrical central section 222. Such a configuration additionally requires less irrigation fluid to prevent charring as the electrode 218 does not contact the tissue directly.

In use, the embodiment from FIG. 5 is used to create a discontinuous helical burn pattern formed of a plurality of discrete burn areas in the tissue. The helical burn pattern is formed during a single treatment session and does not require the device be moved to create the plurality of discrete burn areas.

Figure 10:
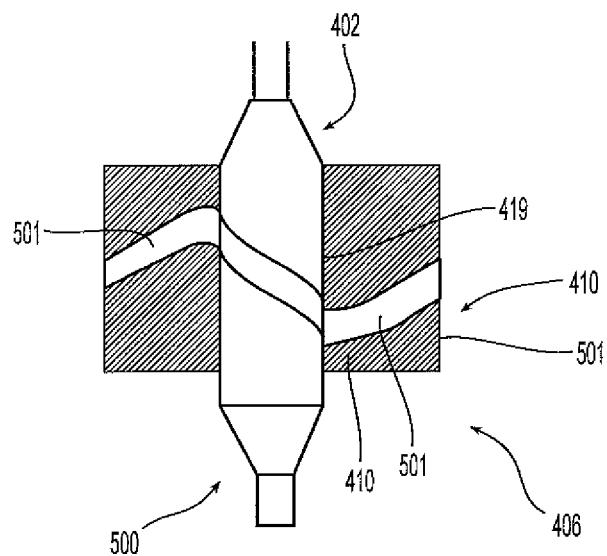
FIG. 10 is illustrates tissue ablation in a general helical pattern caused by an energy delivery device with a helical electrode according to an embodiment of the present disclosure.

FIG. 10 is a photograph of an RF delivery device 410 on top of a piece of heart tissue 500 which has been ablated with RF energy delivered by a device similar to that in FIG. 4 and a system similar to that of FIG. 6. The heart tissue was originally cut as a cylinder into the core of which the distal end 406 of the RF delivery device 410 was deployed. RF energy comprising a signal of 400K Hz at 40 volts and 40 watts was then delivered to the tissue. The cylinder of tissue was then cut along its length so that the inner surface of the tissue cylinder could be visualized. Helical burn zone 501 was created by helical electrode 419. The burn zone has the same configuration as the helical electrode.

Figure 11A:
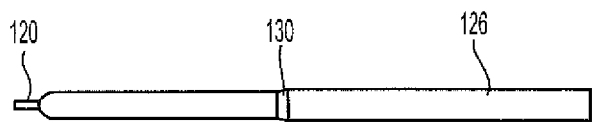
FIGS. 11A-11H illustrate a method of manufacturing an energy delivery device with a helical electrode on an expandable element according to an embodiment of the present disclosure.
Figure 11B:
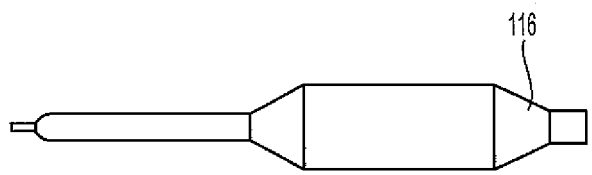

One aspect of the disclosure is a method of manufacturing RF delivery devices. FIGS. 11A-11H illustrate a method of manufacturing a portion of the RF delivery device 110 from FIG. 4. In FIG. 11A, catheter 126 is provided and can be any suitable catheter or other elongate device, such as a sheath. For example, catheter 126 can be an extruded material, and optionally can have a stiffening element therein such as a braided material. In this embodiment catheter 126 is extruded with a guide element lumen and an irrigation lumen formed therein (not shown), and the irrigation port is formed therein (not shown). The irrigation lumen is closed off at the distal end of the catheter to prevent fluid from escaping the distal end of catheter, but the irrigation lumen can stop at the irrigation port rather than continuing further towards the distal end.

Figure 11C:
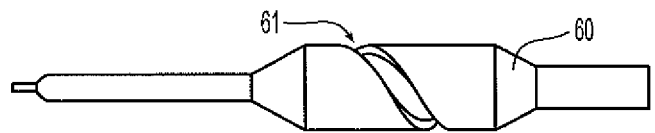
Figure 11D:
Figure 11E:
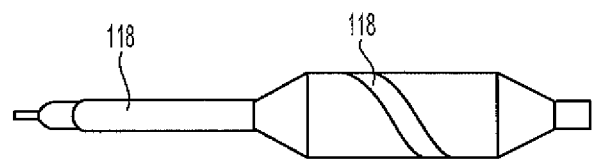
Figure 11F:
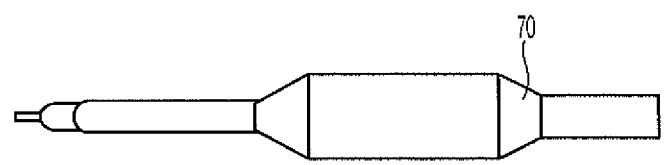
Figure 11G:
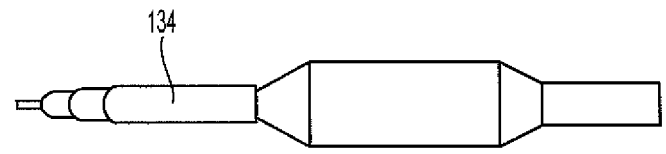
Figure 11H:
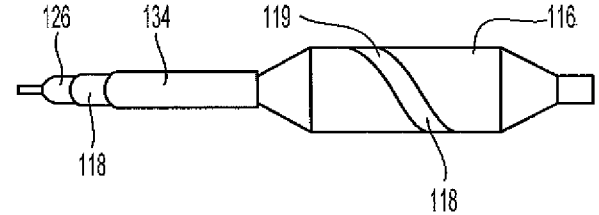

Inflatable element 116, which can be an inflatable balloon, is then secured to the exterior of catheter 126 using any suitable technique such that irrigation port 130 is disposed within inflatable element 116. Next, mask 60 is applied or slid over inflatable element 116. The mask is configured such that it covers areas where the conductive material is not to be deposited and is open where conductive material is to be applied. In FIG. 11C, mask 60 is configured with open area 61 to allow for the deposition of a conductive element 118 in a helical configuration. Inflatable element 116 is then inflated with a suitable inflation fluid (e.g., liquid or gas) delivered through the irrigation lumen and out port 130 to expand, or inflate, inflatable element 116, as shown in FIG. 11C. Additionally, mask 60 is typically configured to mask the distal transition section of the expandable portion and the catheter distal to the expandable portion. After mask 60 is applied, conductive material 118 is then deposited, in a single deposition step, onto substantially all of catheter 126, portions of inflatable element 116, and mask 60. This forms a conductive material layer on substantially all of catheter 126, proximal portion of inflatable element 116, and in the helical pattern on inflatable element 116. After the conduction material 118 is deposited in the single step and allowed to dry sufficiently and or cure, inflatable element 116 is deflated and the mask 60 is removed. As shown in FIG. 11F, a second mask 70 is then applied over those areas of conductive material 118 which are intended to deliver energy directly to the tissue in the energy delivery pattern, which is the helical pattern. The inflatable element 216 is then reinflated and insulation material 134 is applied to substantially the entire device in a single depositing step as shown in FIG. 11G. This forms an insulation layer on substantially the entire conductive material already deposited on catheter 126, the proximal portion of the inflatable element, and the intermediate portion of the inflatable element where mask 70 is not disposed. Next, after appropriate drying and or curing the inflatable element is deflated and the mask 70 removed as shown in FIG. 11H. After mask 70 is removed, shaft 126 and proximal transition section of inflatable element is encapsulated by conductor 118 which are in turn encapsulated by dielectric 134, while helical conductive electrode 118 on the inflatable element is not covered with dielectric. The irrigation apertures are then formed, such as by laser drilling.

In some embodiments of manufacturing the device, the layers of conductive material and insulation material are between about 0.0001 and about 0.001 inches thick. In some embodiments the conductive layer is about 0.0003 inches thick. In some embodiments the insulation layer is about 0.0005 inches thick.

Alternate methods for deposition of the conductor and/or the dielectric layers that can be used and do not require masking include ink jet and or pad printing techniques.

These methods of manufacturing form a unitary conductor. A "unitary conductor" as described herein is a single conductive material comprising both a conduction element and an electrode element wherein the conductive element communicates energy between the controller and the electrode element.

The conductive and insulation materials can each be deposited on substantially all of elongate portion 112 (excluding the portion within expandable portion 114) and expandable portion 114 in a single step, reducing the time necessary to form the conductive and insulation layers, respectively. This can also simplify the manufacturing process. To deposit the conductive and insulation material, the device can be secured to a mandrel and spun while the material is deposited, or the device can be secured in place while the device used to deposit the material is moved relative to the device, or a combination of the two steps. "Single step" as used herein includes a step that applies the material without stopping the deposition of material. For example, the conductive material can be deposited on substantially all of the catheter proximal to the inflatable element and to the inflatable element in a single step. "Single step" as used herein also includes applying a second or more coats to the elongate portion and the expandable portion after initially ceasing the deposition of material. For example, a process that applies a first coat of conductive material to substantially all of the catheter proximal to the inflatable element and to the inflatable element, followed by a ceasing of the deposition, but followed by application of a second coat to substantially the entire portion of the catheter proximal to the inflatable element and to the inflatable element, would be considered a "single step" as used herein. Some previous attempts to form a conductive material on an elongate device formed one or more discrete conductive elements on the elongate device, thus complicating the deposition process. These and other attempts failed to appreciate being able to form a single layer of conductive material on substantially all of the catheter or other elongate device. These attempts failed to appreciate being able to form single layer of conductive material on the catheter and an electrode element on an expandable element in a single step.

By disposing the conductive material on the external surfaces of the catheter and inflatable element in a single step, the creation of electrical junctions is avoided. For example, a junction need not be formed between the conductive material on the catheter and the conductive material on the inflatable element. As used herein, electrical junction refers to a connection created between two conductive materials, either the same or different materials, that allows an electrical signal to be conducted from one material to the other.

The inflatable element is, in some embodiments, an inflatable balloon that is adapted to be inflated upon the delivery of a fluid through the irrigation lumen and out of the irrigation port. In the embodiment in FIGS. 1-11, the inflatable element is a balloon made of non-elastic, or non-compliant, material, but it can be a compliant, or elastic, material as well. Materials for a non-compliant balloon include, without limitation, polyethylene, polyethylene terephthalate, polypropylene, cross-linked polyethylene, polyurethane, and polyimide. Materials for a compliant balloon include, without limitation, nylon, silicon, latex, and polyurethane.

In some embodiments of the embodiment in FIG. 4, the length of the cylindrical intermediate portion of the inflatable element is between about 1 cm and about 4 cm. In some embodiments the inflatable element has a diameter between about 4 mm and about 10 mm. In some particular embodiments the length of the intermediate portion of the inflatable element is about 20 mm and the diameter is about 5 mm to about 7 mm.

The conductive material can be deposited onto the catheter and/or expandable portion. Methods of depositing include, without limitation, pad printing, screen printing, spraying, ink jet, vapor deposition, ion beam assisted deposition, electroplating, electroless plating, or other printed circuit manufacturing processes.

In some embodiments the conductive material deposited is an elastomeric ink and the dielectric material is an elastomeric ink. They can be sprayed on the respective components. In some embodiments the elastomeric ink is diluted with an appropriate diluent to an appropriate viscosity then sprayed in a number of coats while the delivery device is rotated beneath a linearly translating spray head.

Conductive materials that can be deposited on the device to form one or more conductive layers of the device include conductive inks (e.g., electrically conductive silver ink, electrically conductive carbon ink, an electrical conductive gold ink), conductive powders, conductive pastes, conductive epoxies, conductive adhesives, conductive polymers or polymeric materials such as elastomers, or other conductive materials.

In some embodiments the conductive material comprises an elastomeric matrix filled with conductive particles. Elastomeric components include silicones and polyurethanes. Conductive materials are conductive metals such as gold or silver. Conductive inks that can be used are conductive ink CI-1065 and CI-1036 manufactured by ECM of Delaware Ohio. This ink is an extremely abrasion resistant, flexible, and highly conductive elastomeric ink. The ink has the following properties: 65% solids in the form of silver flakes; 0.015 ohms/square (1 mil (0.001 inches) thick); and a 10 minute cure time at 248 F.

The electrodes described herein can also be used as a temperature sensor. Ablative electrodes are routinely used in wide variety of surgical procedures. Many of these procedures are performed percutaneously, and a subset are performed endovascularly. In many of these procedures it is customary to incorporate provisions to monitor the temperature of the ablative electrodes. This temperature information is then used in some fashion as an input in a control scheme to limit the maximum temperature the electrode is allowed to attain. In this fashion a number of mechanisms, that may be deleterious to the desired outcome, may be controlled and or limited. Some of these effects, which in some circumstances are considered deleterious are, tissue charring, creation of steam, and the resultant uncontrolled, rapid, or large changes in interface impedance.

The temperature monitoring is typically carried out by incorporating and mounting some form of a temperature sensor such as a thermocouple, an rdt, or a thermistor in proximity to, or on, the electrode.

The electrodes are typically comprised of metals or metal alloys which are either deposited as metals directly through various metal deposition procedures such as, but not limited to physical or chemical metal vapor deposition, or applied as a component in a matrix such as but not limited to organic polymers in the form of an ink. Such inks are deposited in many ways, a few of which are, screening, spraying, ink jetting.

Metals, metal alloys, and other metal compound have resistance characteristics which are dependent on temperature, typically called the temperature coefficient of resistance or "tempco." The magnitude and characteristics of these effects varies and is often used in devices such as a resistance temperature detector "RTD", such as a platinum rtd's, or in positive temperature coefficient "PTC" or negative temperature coefficient "NTC" thermistors.

The systems herein can therefore alternatively monitor temperature by using the inherent tempco of the electrode itself as a way of monitoring its temperature and or controlling its impedance and thereby self-limiting its power output and thereby its temperature.

Figure 12:
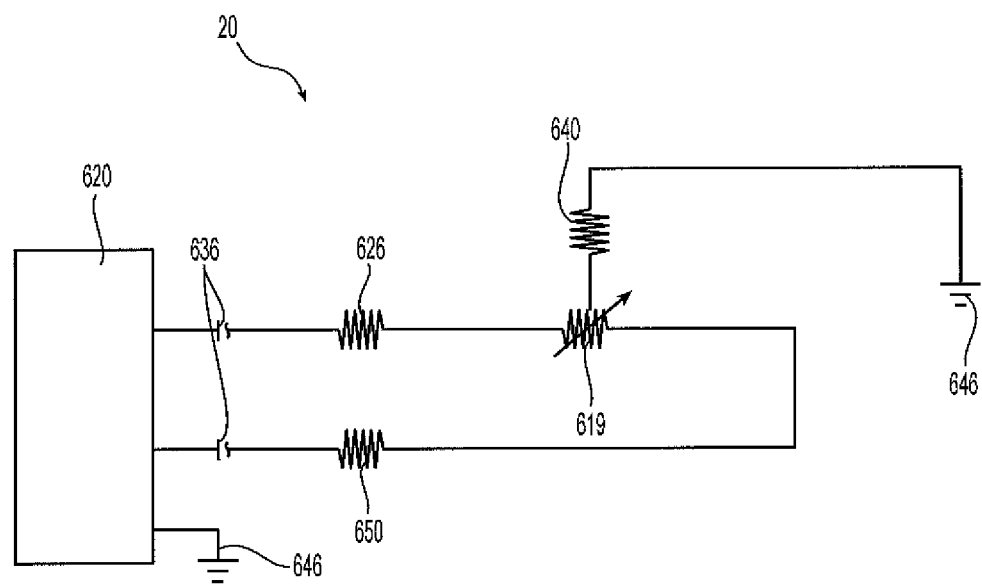
FIG. 12 represents an embodiment of a system similar to that of FIG. 6 represented by the resistances of the various elements according to an embodiment of the present disclosure.

FIG. 12 represents an embodiment of a system similar to that of FIG. 6 represented by the resistances of the various elements. The delivery RF lead which runs down the catheter is represented as resistance 626 and the electrode is represented by resistance 619. In this embodiment there is an additional conductive element running along the catheter shaft which is a return line represented by resistance 650. In use the leads whose resistances are represented by 626 and 650 may be sourced in parallel when RF is delivered to electrode 619 and addressed separately when used to characterize the resistance and hence temperature of the electrode 619. Alternatively one of them may be used solely for the purpose of monitoring temperature and therefore left open circuited when RF is being delivered. The design of the delivery system and electrode will be such that the impedance 640 of the patient will be orders of magnitude greater than the impedances for the delivery leads 626, 650, and the electrode 619. In one embodiment impedance 619 will be considerably greater than 626 or 650, or in some cases the parallel combination of 626 and 650.

In one embodiment the electrode is comprised of a layer of platinum and the temperature of the electrode may be characterized by monitoring the voltage drop across the series resistances 626, 619, 650. This may be done intermittently, interspersed in the delivery of the RF energy. As the electrode heats, its resistance will increase in a well-known and repeatable fashion. As the leads 626 and 650 have lower resistance and will not self-heat appreciably, the change in resistance will be primarily due to the heating of electrode 619 and variation in its resistance. Many other scenarios will be understood to those skilled in the art.

An alternate arrangement which relies on the use of a PTC for the electrode relies on the rapid change in resistance of the electrode past a particular set point which is a function of the composition of the electrode. In this configuration the tempco of the electrode is relatively small, for example, below about 40 C but above about 40 C. In this temperature range the tempco rapidly increases thereby limiting delivered power in a voltage-limited RF configuration. Many alternate embodiments will be understood by those skilled in the art.

Figure 13:
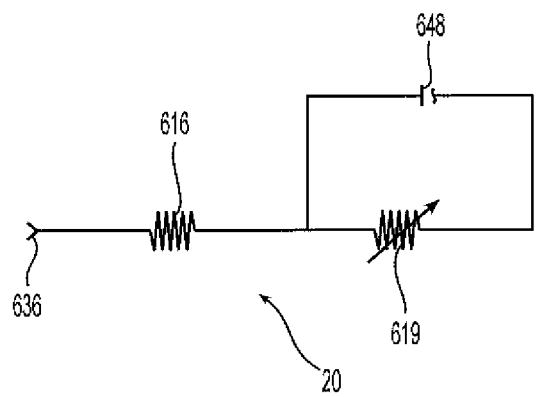
FIG. 13 illustrates an alternative configuration in which a capacitor, inductor, or both may be incorporated in the circuit from FIG. 12.

FIG. 13 illustrates an alternative configuration in which a capacitor 648, inductor (not shown), or both may be incorporated in the circuit. In one embodiment the circuit may incorporate only one source lead and the inherent resonance of the circuit which will depend on the varying impedance of the electrode resistance.

In yet another alternative the tempco associated with a conductive ink such as the ECM CI-1036 may be used. Experimentally the ECM CI-1036 demonstrated a 0.1% increase in impedance per degree over the range of 30 C to 60 C.

Figure 16:
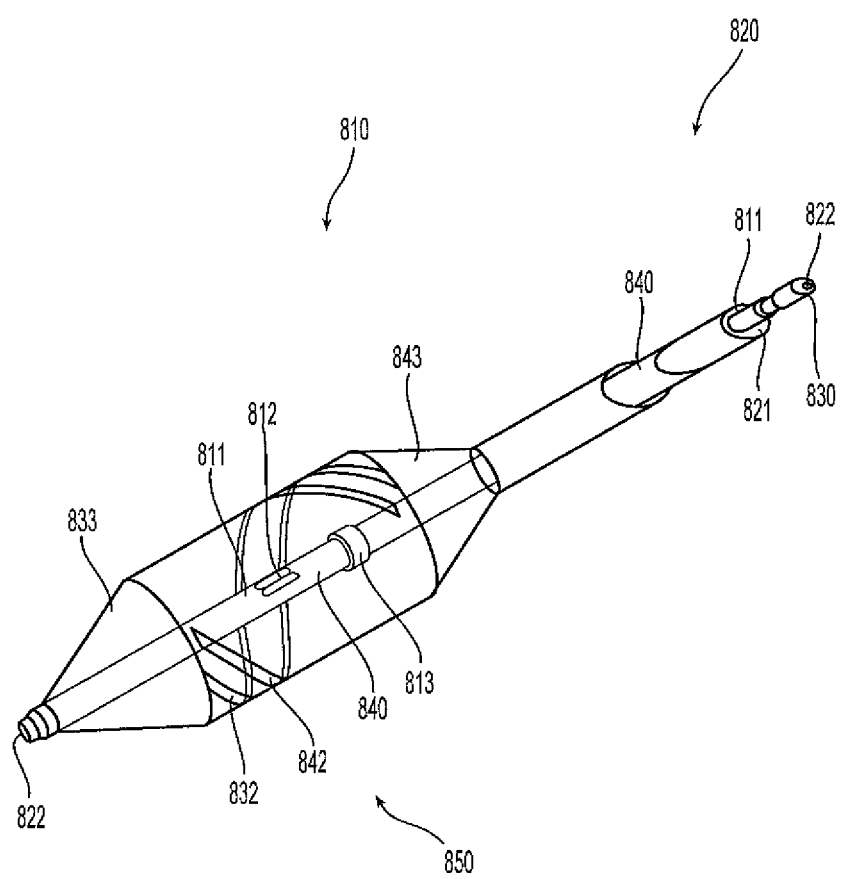
FIG. 16 illustrates a portion of an energy delivery device including a helical electrode pair on an expandable element according to another embodiment of the present disclosure.

As described above, devices capable of ablating renal nerves surrounding the renal arteries are useful in treating hypertension. The device disclosed in FIG. 16 is another embodiment of a device adapted for such purpose. The device described herein comprises a bipolar electrode pair disposed on the outer surface of an expandable structure comprised of an inflatable balloon. A bipolar electrode pair provides for both a more controlled burn and a shallower burn than a comparable monopolar electrode. The device is configured for endovascular delivery to a renal artery. Each of the individual electrodes comprising the bipolar set is in turn comprised of a unitary electrode/conductor.

Referring to FIG. 16, detailed description of the distal features of an embodiment of the device is as follows. The distal portion of an bipolar RF delivery device 810 includes an expandable section 850 including a balloon, and a catheter shaft section 820 including an inner shaft 830 and an outer shaft 840. The inner lumen of the inner shaft 830 includes a guidewire lumen 822. The annular gap between the inner and outer shafts includes an irrigation lumen 821. The outer shaft 840 also includes an irrigation outflow 812 (e.g., an irrigation port) located near its distal end such that it is disposed within the balloon. A temperature sensor 811 may be located within the balloon 850 and interconnecting leads of the temperature sensor 811 may be routed through the irrigation lumen outflow 812 and irrigation lumen 821.

Prior to assembly, a conductive material is deposited on substantially the entire inner shaft 830. A dielectric material is then deposited on the conductive material except at the distal most end of the inner shaft 830. The inner shaft 830 is then fitted within the outer shaft 840 and the two are affixed to one another such that the inner shaft 830 extends beyond the most distal portion of the outer shaft 840 and the balloon 850. The dielectric on the inner shaft 830 is deposited on at least the portions of the surface of the conductor on the inner shaft 830 that would contact irrigation fluid, thus preventing the conductive material on the inner shaft 830 from coming into contact with irrigation fluid. The distal end of the inner shaft 830, which extends distal to the outer shaft 840, is not coated with dielectric. This allows the inner shaft 830 to be in electrical communication with the inner sourced electrode as described below.

Next, the outer shaft 840 and balloon 850 are coated with an elastomeric ink, and then, subsequently, by a dielectric as described above. The conductive coating is deposited on the outer shaft 840, all or a portion of the proximal cone 843 of the balloon 850, and on the balloon 850, forming a conductive material that includes an outer sourced spiral electrode 842. This conductive material can be deposited in a unitary manner, as is described above and in the materials incorporated by reference herein. Conductive material is also deposited on the most distal section of the shaft assembly, the distal cone portion 833 of the balloon 850, and the balloon 850, forming a conductive material that includes an inner sourced electrode 832. This conductor can also be formed in a unitary manner. The conductive material that forms the inner sourced electrode can be the same material that is used for the outer sourced electrode. When the distal conductor (which includes the inner sourced electrode 832) is formed, it interfaces electrically with the conductor on the inner shaft 830 that extends distal to the balloon 850. The conductive materials can be selected such that when the conductive materials are deposited, the interface is a single layer of the same material rather than two distinct layers. The conductor and dielectric structures can be fabricated as described above. When used in bipolar mode, energy passes from one spiral electrode 832 or 842, through renal nerve tissue, to the other electrode. The electrodes 832, 842 can be used in a bipolar manner, or each electrode can be used in monopolar mode. Bipolar mode can be used if the tissue burn need not be as deep as may be needed if using a monopolar mode. Bipolar mode generally allows more control in the tissue burn. Additionally or alternatively, the electrodes 832, 842 can be used together as a single monopolar electrode (e.g., by feeding both electrodes with the same frequency and RF energy such that the electrodes appear to be one electrode).

In an alternative embodiment, the inner shaft is not coated with a conductor (or dielectric) and, instead, a wire extends through the irrigation lumen, and interfaces the conductor that includes the inner sourced electrode.

Although not shown in FIG. 16, irrigation ports as described above can be situated such that they pass through the electrode structures, sit adjacent to the electrode structures such as in the space between them or exterior to the pair, or both.

One or more radio opaque markers 813 may be affixed to the outer shaft.

Figure 17:
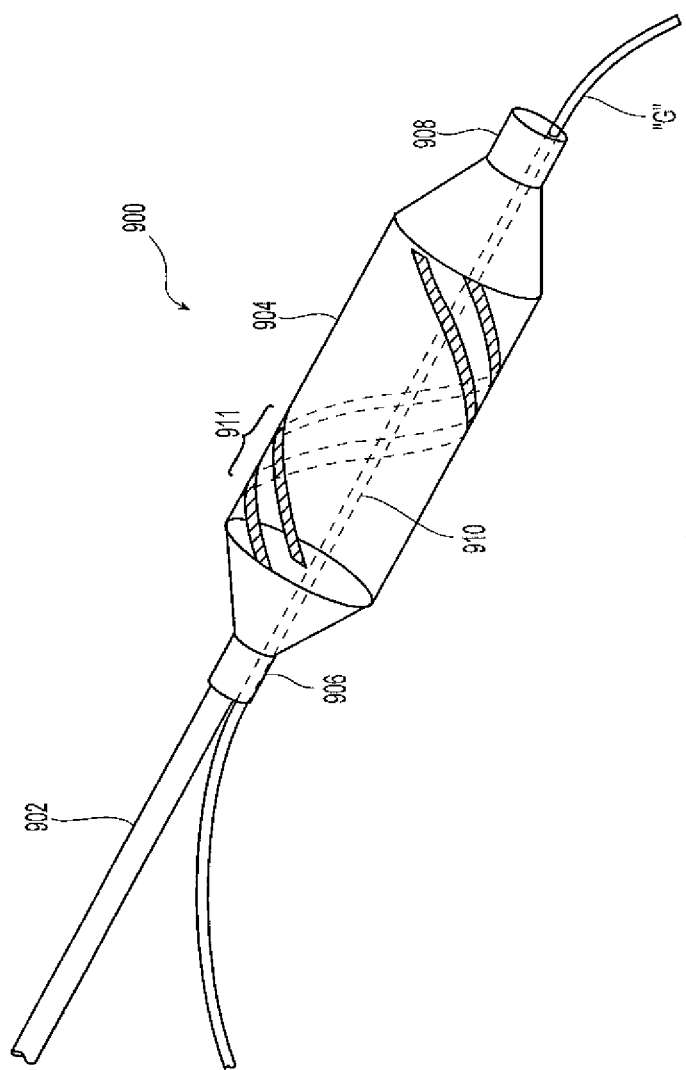
FIG. 17 illustrates a perspective view of an energy delivery device having a rapid exchange configuration according to another embodiment of the present disclosure.

In the embodiments described hereinabove, the RF delivery devices are suitable for use in over-the-wire catheter systems. As shown in FIG. 17, embodiments of the RF delivery device may be configured for use in a rapid exchange catheter system. Turning to FIG. 17, RF delivery device 900 includes a catheter shaft 902. The proximal end of the catheter shaft 902 is connected to an RF generator (not shown) and a fluid reservoir (e.g., fluid reservoir 326 of FIG. 6). The distal end of the catheter shaft 902 terminates within an inflatable element or balloon 904. The catheter shaft 902 fluidly couples a chamber defined by the balloon 904 with the fluid reservoir. The balloon 904 extends from the proximal hub 906 to the distal hub 908. A guidewire lumen 910 extends from the proximal hub 906 to the distal hub 908 and is configured and dimensioned to receive a guidewire "G". The balloon 904 has a pair of helical electrodes 911 that make about 1 revolution around the balloon 904.

The RF delivery device 900 is delivered to a treatment zone (e.g., the renal artery) by passing guidewire lumen 910 of RF delivery device 900 over a guidewire "G" previously positioned in the appropriate location within the vascular system. The balloon 904 is then inflated by irrigation fluid from the fluid reservoir via the catheter shaft 902. RF energy from the RF generator is then applied to the vascular tissue via the pair of helical electrodes 911. After application of the RF energy, the balloon 904 is deflated and RF delivery device 900 is removed from the patient.

RF delivery device 900 will be described in more detail while making reference to FIGS. 18 through 19D. The balloon 904 includes a proximal transition section 912, an intermediate section 914, and a distal transition section 916. The proximal transition section 912 and the distal transition section 916 are shown with conical configurations but are not limited to these configurations. The intermediate section 914 is substantially cylindrically-shaped when the balloon 904 is in the expanded configuration shown in FIG. 18. The proximal end of the balloon 904 is secured to the proximal hub 906 and the distal end of the balloon 904 is secured to the distal hub 908.

The pair of helical electrodes 911 includes a first helical electrode 920 and a second helical electrode 922 that are electrically coupled to the RF generator. The first helical electrode 920 and the second helical electrode 922 make about 1 revolution around the balloon 904. In other embodiments, the first helical electrode 920 and the second helical electrode 922 make about 0.5 to about 1.5 revolutions around the balloon 904. The first helical electrode 920 and the second helical electrode 922 are fabricated from one or more of the conductive materials described above.

FIG. 19A illustrates a cross-section of the catheter shaft 902 taken along the section line 19A-19A shown in FIG. 18. The catheter shaft 902 includes an irrigation shaft 924 that defines an irrigation lumen 926. Irrigation lumen 926 fluidly couples the fluid reservoir to the balloon 904. A first conductive layer 928 is fabricated from a conductive material and disposed about the irrigation shaft 924. A first insulation layer 930 fabricated from an insulation material is disposed about the first conductive layer 928. A second conductive layer 932 fabricated from a conductive material is disposed about the first insulation layer 930. The first insulation layer 930 prevents a short circuit between the first conductive layer 928 and the second conductive layer 932. A second insulation layer 934 is disposed about the second conductive layer 932. The second insulation layer 934 protects vascular tissue and blood from the RF energy flowing through the second conductive layer 932. The first conductive layer 928 and the second conductive layer 932 are electrically coupled to the RF generator.

FIG. 19B illustrates a cross-section of the proximal hub 906 taken along the section line 19B-19B shown in FIG. 18. As shown in FIG. 19B, the irrigation shaft 924 having the first conductive layer 928 disposed thereon is positioned within a proximal section 936a of a rapid exchange shaft 936. The rapid exchange shaft 936 defines the guidewire lumen 910. A proximal end 938 of balloon 904 is secured to the proximal section 936a of the rapid exchange shaft 936. A proximal transition conductive region 940 is fabricated from a conductive material and disposed about the proximal end 938 of balloon 904. As will be described below, second conductive layer 932 is electrically coupled to the proximal transition conductive region 940 which, in turn, is electrically coupled to the first helical electrode 920, electrically coupling the RF generator to the first helical electrode 920. A proximal insulation layer 942 is disposed about the proximal transition electrode 940.

FIG. 19C illustrates a cross-section of the intermediate section 914 of the balloon 904 taken along the section line 19C-19C shown in FIG. 18. An intermediate portion 936b of the rapid exchange shaft 936 extends from the proximal section 936a to a distal section 936c (FIG. 19D). Disposed about the intermediate portion 936b is a third conductive layer 944 and third insulation layer 946. The third insulation layer 946 isolates the third conductive layer 944 from the irrigant used to inflate the balloon 904 to prevent RF energy from being conducted through the irrigant. The balloon 904 defines a chamber 948 configured to receive irrigant from the fluid reservoir. When irrigant is pumped into the chamber 948, the intermediate section 914 of the balloon 904 assumes its expanded configuration having a substantially cylindrical shape. When irrigant is pumped out of or removed from the chamber, the intermediate section 914 of the balloon 904 assumes its unexpanded configuration.

FIG. 19D illustrates a cross-section of the distal hub 908 of the RF delivery device 900 taken along the section line 19D-19D shown in FIG. 18. Distal section 936c of the rapid exchange shaft 936 is coated with the third conductive layer 944 and the third insulation layer 946. A distal end 950 of balloon 904 is secured to the third insulation layer 946. Disposed about the distal end 950 of balloon 904 is a distal transition electrode 952. As will be described in detail below, the distal transition conductive region 952 electrically couples second helical electrode 922 to the third conductive layer 944 which, in turn, is electrically coupled to first conductive layer 928, electrically coupling the RF generator to the second helical electrode 922. A distal insulation layer 954 is disposed about the distal transition electrode 952.

Figure 20F:
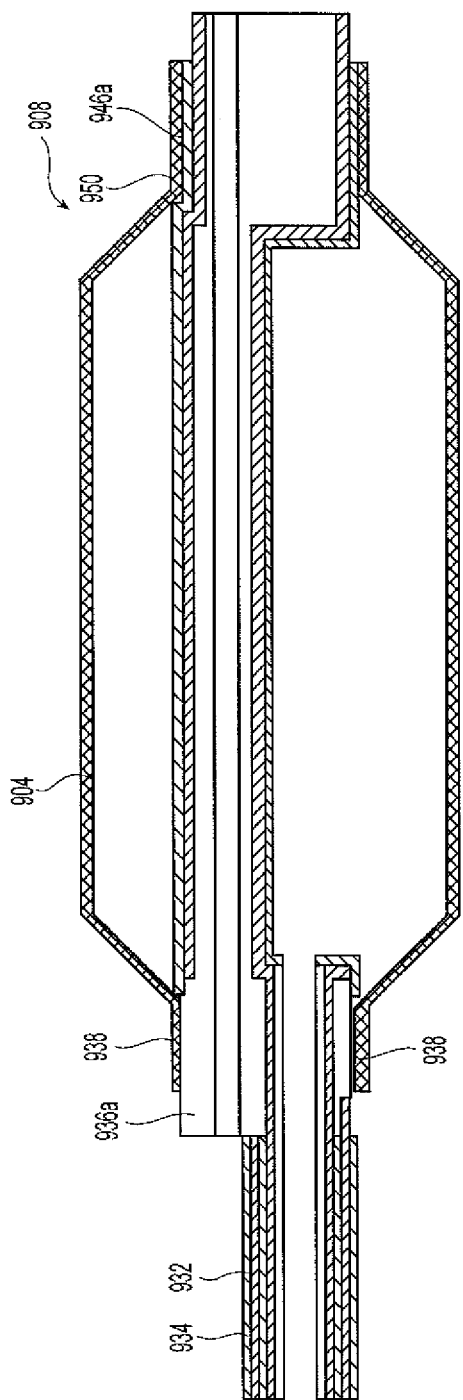

FIGS. 20A through 20H illustrate a method of manufacturing the RF delivery device 900. The conductive layers and insulation layers described below are applied using any of the methods described hereinabove. As shown in FIG. 20A, irrigation shaft 924 has the first conductive layer 928 applied thereon. The first insulation layer 930 is applied to the first conductive layer 928. As shown in FIG. 20B, the distal portion 928a of the first conductive layer remains exposed after the first insulation layer 930 is applied. The proximal section 936a of the rapid exchange shaft 936 is attached to the catheter shaft 902 such that the proximal section 936a insulates a substantial part of the distal portion 928a of the first conductive layer 928. (See FIG. 20C.)

As shown in FIG. 20D, the second conductive layer 932 is disposed proximally from the rapid exchange shaft 936 about the first insulation layer 930. The third conductive layer 944 is disposed about the intermediate section 936b and the distal section 936c of the rapid exchange shaft 936. The third conductive layer 944 is electrically coupled to the first conductive layer 928. Additional insulation layers are applied to the RF delivery device 900 as shown in FIG. 20E. For instance, the second insulation layer 934 is disposed proximally from the rapid exchange shaft 936 about the second conductive layer 932. The third insulation layer 946 is disposed about the third conductive layer 944. A distal portion of the third conductive layer 944 remains exposed after the third insulation layer 946 is applied.

As shown in FIG. 20F, the balloon 904 is attached to the RF delivery device 900. For example, in some embodiments, the proximal end 938 of balloon 904 is attached to the proximal section 936a of the rapid exchange shaft 936. The proximal end 938 is attached to the proximal section 936a by conventional means. The distal end 950 of balloon 904 is attached to a distal end 946a of the third insulation layer 946. After the balloon 904 is attached to the RF delivery device 900, the proximal transition electrode 940, the first helical electrode 920, the second helical electrode 922, and the distal transition conductive region 952 is added by any of the methods described above.

Figure 20G:
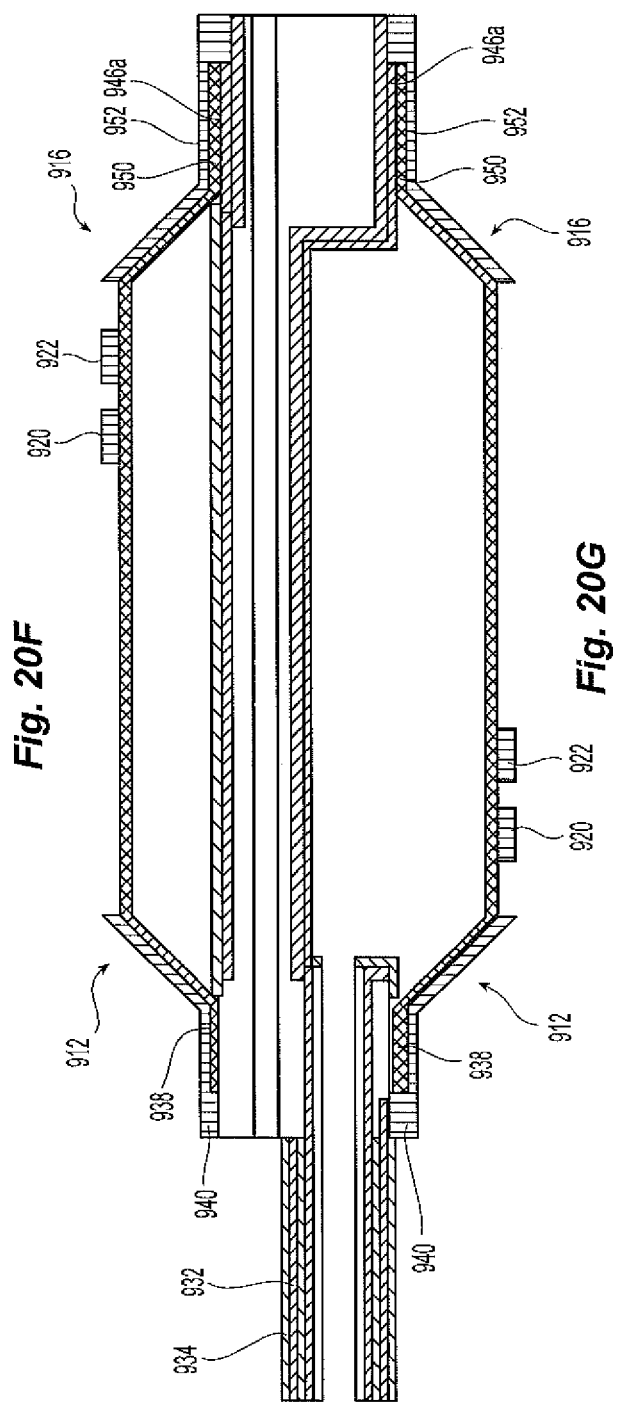

For instance, as shown in FIG. 20G, the conductive material that forms the proximal transition electrode 940 is applied over the proximal end 938 and the proximal transition section 912 of balloon 904 and is electrically coupled to the second conductive layer 932. The proximal transition conductive region 940 electrically couples the second conductive layer 932 to the first helical electrode 920. The conductive material that forms the distal transition conductive region 952 is applied over the distal transition section 916 and the distal end 950 of balloon 904 and is electrically coupled to the third conductive layer 944. The distal transition conductive region 952 electrically couples the third conductive layer 944 to the second helical electrode 922.

Figure 20H:
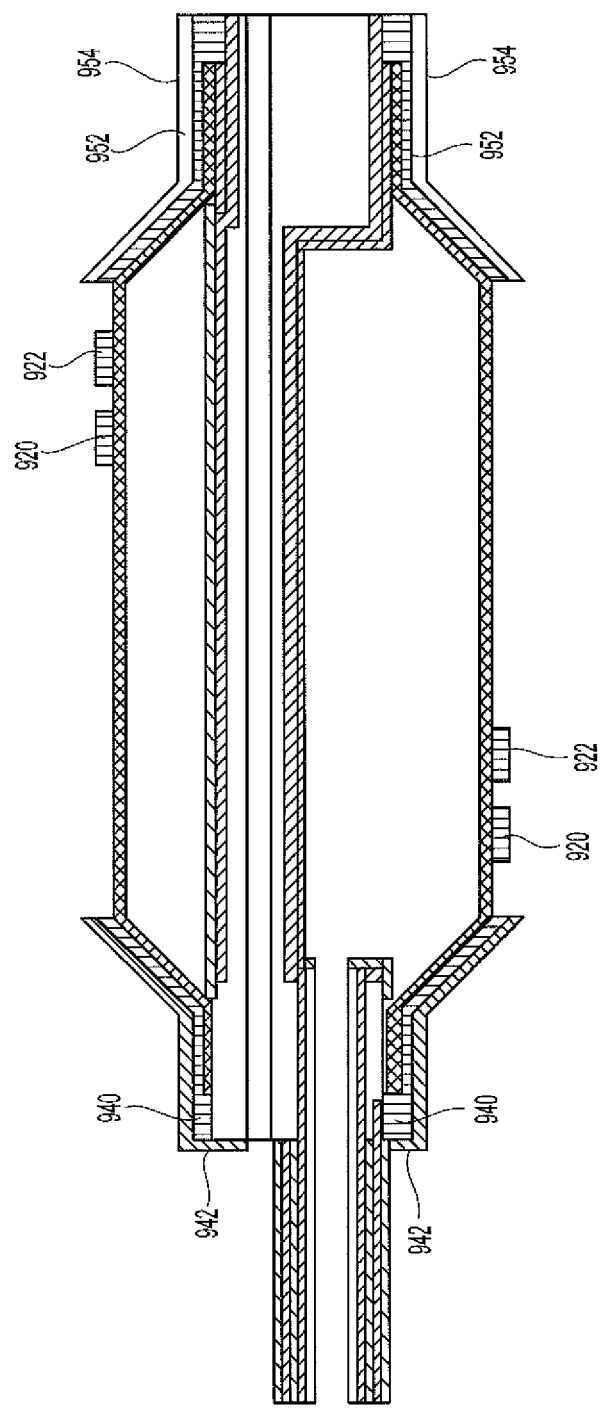

As shown in FIG. 20H, insulation layers are disposed about the proximal transition conductive region 940 and the distal transition conductive region 952 by conventional means. For example, the proximal insulation layer 942 is applied over the proximal transition conductive region 940 and the distal insulation layer 954 is applied over the distal transition conductive region 952 to insulate the proximal transition conductive region 940 and the distal transition conductive region 952 from the surrounding tissue. The first helical electrode 920 and the second helical electrode 922 remain exposed in order to apply RF energy to a treatment zone within the vascular system.

The RF delivery device 900 may be used in a bipolar mode where RF energy travels between the first helical electrode 920 and the second helical electrode 922. Alternatively, the RF delivery device 900 may be used in a monopolar mode where RF energy is delivered, optionally simultaneously, by the first helical electrode 920 and the second helical electrode 922, and the circuit is completed by an external return electrode (e.g., grounding plates 340 of FIG. 6).

Although not shown in FIGS. 17-20H, irrigation ports as described above can be situated such that they pass through the first helical electrode 920 and/or the second helical electrode 922, sit adjacent to the electrode structures, e.g., in the space between the first helical electrode 920 and the second helical electrode 922 or exterior to the first helical electrode 920 and the second helical electrode 922, or both.

Figure 21:
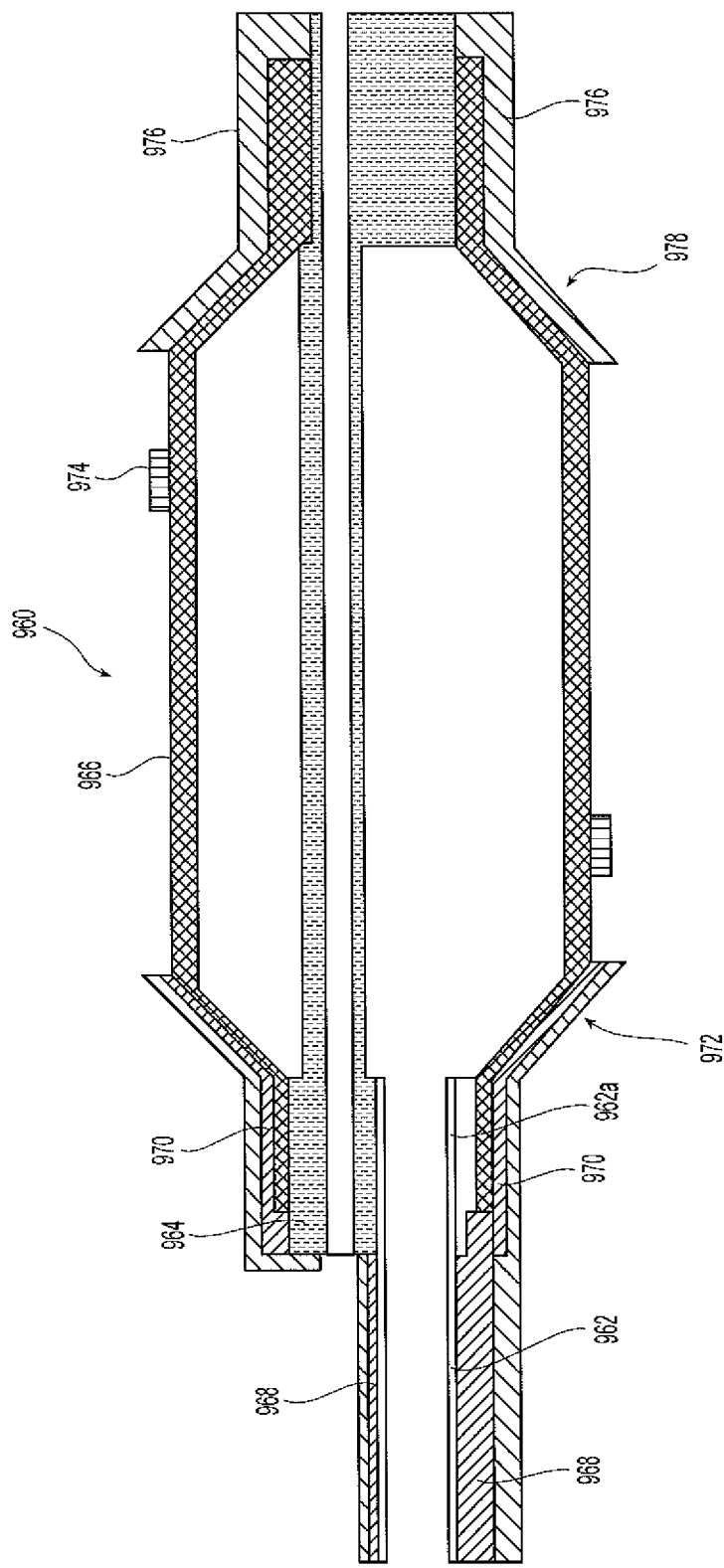
FIG. 21 illustrates a cross-sectional view of an energy delivery device having a rapid exchange configuration according to another embodiment of the present disclosure.

The rapid exchange configuration may also be used for an RF delivery device having a single helical electrode. For example, as shown in FIG. 21, RF delivery device 960 includes an irrigation shaft 962 and a rapid exchange shaft 964 coupled to a distal end 962a of the irrigation shaft 962. A balloon 966 is attached to the rapid exchange shaft 964 by conventional means. A first conductive layer 968 is disposed about irrigation shaft 962 and is electrically coupled to an RF generator (not shown). A proximal transition electrode 970 is applied to a proximal end 972 of balloon 966. The proximal transition electrode 970 is electrically coupled to helical electrode 974 thereby electrically coupling the RF generator to the helical electrode 974. The helical electrode 974 makes about 0.5 to about 1.5 revolutions around the balloon 966. A polymer layer 976 is applied to a distal end 978 of balloon 966 to secure the balloon 966 to the rapid exchange shaft 964.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. An energy delivery assembly for delivering ablative energy to tissue, the energy delivery assembly comprising:
    an expandable element;
    an electrode that is configured to deliver electrical energy sufficient to ablate target tissue;
    a rapid exchange shaft that defines a guidewire lumen that is configured to receive a guidewire;
    an elongated inner shaft including a proximal portion and a distal portion, wherein the elongated inner shaft includes:
        an irrigation shaft that defines an irrigation lumen that fluidly couples a fluid reservoir and the expandable element, the irrigation lumen and the guidewire lumen being nonconcentric;
        a first conductive layer that covers and is disposed about the irrigation shaft;
        a first insulation layer that covers the first conductive layer;
        a second conductive layer that covers and is disposed about the first insulation layer; and
        a second insulation layer that covers and is disposed about the second conductive layer; and
    a third conductive layer disposed about at least a portion of the rapid exchange shaft.

2. The energy delivery assembly of claim 1 wherein the first conductive layer, the first insulation layer, the second conductive layer, and the second insulation layer extend 360 degrees around the elongated inner shaft.

3. The energy delivery assembly of claim 2 wherein the first conductive layer covers all of the elongated inner shaft, the first insulation layer covers all of the first conductive layer along the elongated inner shaft, the second conductive layer covers all of the first insulation layer along the elongated inner shaft, and the second insulation layer covers all of the second conductive layer along the elongated inner shaft.

4. The energy delivery assembly of claim 1 wherein the electrode has a helical configuration when the expandable element is in an expanded state and has a length that extends helically around an outer surface of the expandable element.

5. The energy delivery assembly of claim 4 further comprising a second electrode having a length that extends helically around the outer surface of the expandable element and is electrically coupled to the second conductive layer.

6. The energy delivery assembly of claim 4, further comprising:
    a proximal transition conductive region that is disposed about a proximal end of the expandable element and is electrically coupled to the second conductive layer and the electrode that extends helically around the outer surface of the expandable element.

7. The energy delivery assembly of claim 1 wherein the expandable element is a balloon.

8. The energy delivery assembly of claim 1, further comprising a sensor coupled to the second conductive layer.

9. The energy delivery assembly of claim 1, wherein the third conductive layer is electrically coupled to the first conductive layer and a distal transition conductive region that is disposed about a distal end of the expandable element and that is electrically coupled to a second electrode, thereby electrically coupling a generator to the second electrode.

10. The energy delivery assembly of claim 1, wherein the third conductive layer is electrically coupled to the first conductive layer.

11. An energy delivery assembly for delivering energy to tissue, the energy delivery assembly comprising:
    an expandable element;
    a guidewire lumen that is configured to receive a guidewire;
    an irrigation shaft that defines an irrigation lumen that fluidly couples a fluid reservoir and the expandable element and that includes a proximal portion and a distal portion, wherein the irrigation lumen and the guidewire lumen are nonconcentric;
    a first conductive material coating the irrigation shaft from the proximal portion to the distal portion;
    a first insulation layer that covers the first conductive material;
    a second conductive material coating the first insulation layer from the proximal portion to the distal portion;
    a second insulation layer that covers the second conductive material;
    a third conductive material disposed about at least a portion of the guidewire lumen; and
    an electrode that is electrically coupled to the first conductive material.

12. The energy delivery assembly of claim 11 wherein the first conductive material is a first thin metal layer and the second conductive material is a second thin metal layer.

13. The energy delivery assembly of claim 12 wherein the first thin metal layer coats a discrete lateral section of a circumferential surface of the irrigation shaft from the proximal portion to the distal portion, and the second thin metal layer coats a discrete lateral section of the first insulation layer from the proximal portion to the distal portion.

14. The energy delivery assembly of claim 13 wherein the first thin metal layer, the first insulation layer, the second thin metal layer, and the second insulation layer are arranged concentrically with respect to each other.

15. The energy delivery assembly of claim 12 wherein the first thin metal layer is coated 360 degrees around a circumferential surface of the irrigation shaft from the proximal portion to the distal portion, and the second thin metal layer is coated 360 degrees around the first insulation layer from the proximal portion to the distal portion.

16. The energy delivery assembly of claim 15 wherein the first thin metal layer, the first insulation layer, the second thin metal layer, and the second insulation layer are arranged concentrically with respect to each other.

17. The energy delivery assembly of claim 11 wherein:
    the first conductive material is coated 360 degrees around a circumferential surface of the irrigation shaft from the proximal portion to the distal portion;
    the second conductive material is coated 360 degrees around the first insulation layer from the proximal portion to the distal portion; and
    the first conductive material, the first insulation layer, the second conductive material, and the second insulation layer are arranged concentrically with respect to each other about the irrigation shaft.

18. The energy delivery assembly of claim 17, further comprising a sensor coupled to the second conductive material.

19. The energy delivery assembly of claim 17, further comprising a second electrode having a length that extends helically around an outer surface of the expandable element and is electrically coupled to the second conductive material.

20. A method of controlling renal function, the method comprising:
- expanding an expandable element in a renal vessel such that an electrode that is disposed on the expandable element contacts a wall of the renal vessel;
- delivering electrical energy to the electrode via a first conductive material that extends along an irrigation shaft that defines an irrigation lumen thereby thermally modulating neural activity, wherein the irrigation lumen and a guidewire lumen are nonconcentric and the first conductive material coats a portion of the irrigation shaft; and
- transmitting electrical signals along a second conductive material arranged concentrically with the first conductive material, wherein the second conductive material coats a portion of a first insulation layer between the first conductive material and the second conductive material and that is covered by a second insulation layer,
- wherein a third conductive layer is disposed about at least a portion of a guidewire shaft that defines the guidewire lumen.

* * * * *